(12) United States Patent
Reedy et al.

(10) Patent No.: US 10,932,902 B2
(45) Date of Patent: Mar. 2, 2021

(54) DYNAMICALLY TUNABLE APODIZED MULTIPLE-FOCUS OPTHALMIC DEVICES AND METHODS

(71) Applicant: Johnson & Johnson Vision Care, Inc., Jacksonville, FL (US)

(72) Inventors: Matthew Reedy, Jacksonville, FL (US); Randall B Pugh, Jacksonville, FL (US); Derek Nankivil, Jacksonville, FL (US); Pere Ventura, Jacksonville, FL (US); Ross Franklin, Jacksonville, FL (US); Adam Toner, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 207 days.

(21) Appl. No.: 16/054,685

(22) Filed: Aug. 3, 2018

(65) Prior Publication Data

US 2020/0038173 A1    Feb. 6, 2020

(51) Int. Cl.
  *G02C 7/02* (2006.01)
  *A61F 2/16* (2006.01)
  *A61F 2/14* (2006.01)
  *G02C 7/08* (2006.01)
  *G02C 7/10* (2006.01)

(52) U.S. Cl.
  CPC .............. *A61F 2/1627* (2013.01); *A61F 2/15* (2015.04); *G02C 7/083* (2013.01); *G02C 7/101* (2013.01)

(58) Field of Classification Search
  CPC ......... A61F 2/1627; A61F 2/15; G02C 7/101; G02C 7/083; G02C 7/044; G02C 7/06; G02C 7/061; G02C 7/063; G02C 7/065; G02C 7/066; G02C 7/068

USPC ..................................................... 351/159.41
See application file for complete search history.

(56) References Cited

U.S. PATENT DOCUMENTS

| | | | |
|---|---|---|---|
| 4,601,545 A | 7/1986 | Kern | |
| 5,712,721 A | 1/1998 | Large | |
| 6,888,613 B2 | 5/2005 | Robins et al. | |
| 7,404,637 B2 | 7/2008 | Miller et al. | |
| 7,753,521 B2 | 7/2010 | Wooley et al. | |
| 7,926,940 B2 | 4/2011 | Blum et al. | |
| 8,215,770 B2 | 7/2012 | Blum et al. | |
| 8,960,898 B1 | 2/2015 | Etzkorn et al. | |
| 2011/0304530 A1 | 12/2011 | Yeh et al. | |

FOREIGN PATENT DOCUMENTS

| | | |
|---|---|---|
| WO | 2008/078320 A2 | 7/2008 |
| WO | 2012/051223 A2 | 4/2012 |
| WO | 2015/001120 A1 | 1/2015 |
| WO | 2017/105677 A1 | 6/2017 |

OTHER PUBLICATIONS

PCT Search Report Appication No. PCT/IB2019/056545 dated Feb. 19, 2020.

*Primary Examiner* — William R Alexander
*Assistant Examiner* — Henry A Duong

(57) ABSTRACT

Tunable apodized multiple-focus ophthalmic devices and methods characterized by a lens with multiple optical zones each with an optical power optimized for one or more focal lengths and a tunable apodization mask positioned within at least a portion of the optical zone(s). Upon a desired change of focus for the wearer, an optical transmission characteristic of the tunable apodization mask may be varied. The tunable apodization mask may take the form of an electrochromic device or another suitable material.

19 Claims, 13 Drawing Sheets

Intermediate

Near

Distance

⊠ Apodized
☐ Distance zone
▨ Intermediate zone
▨ Near zone

Power Profile

Luminance = 42 cd/m^2

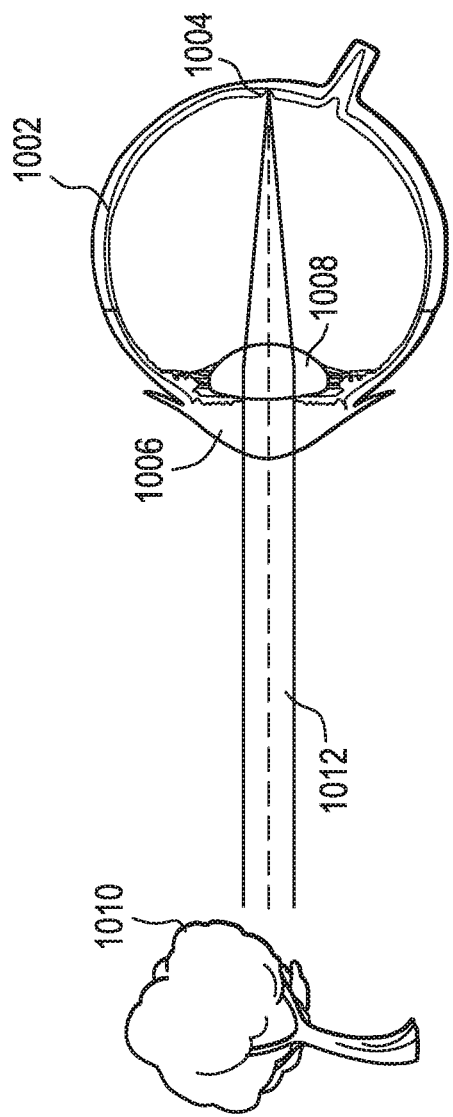
FIG. 10A
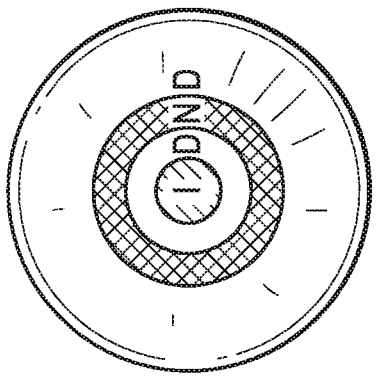
Focused at Distance
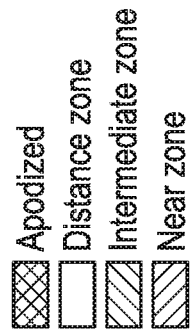
- Apodized
- Distance zone
- Intermediate zone
- Near zone Focused at Near

DYNAMICALLY TUNABLE APODIZED MULTIPLE-FOCUS OPTHALMIC DEVICES AND METHODS

I. BACKGROUND OF THE INVENTION a. Field of the Invention

The present invention relates to electronic ophthalmic devices, such as wearable lenses, including contact lenses, implantable lenses, including intraocular lenses (IDLs) and any other type of device comprising optical components, and more particularly, to methods, systems, and apparatuses for providing an energized ophthalmic device having a tunable apodization mask and multiple-focus lens that operate to enhance the visual performance of the wearer, particularly in individuals affected by presbyopia.

b. Background and Discussion of the Related Art

As an individual ages, the eye is less able to accommodate, i.e., change the optical power of the eye to focus on objects that are relatively near the observer. This loss of the ability to focus with age is known as presbyopia. In its extreme form, e.g., in a mature presbyope or a person who has had their natural lens removed and an intraocular lens inserted as a replacement, the ability to accommodate may be completely absent. Numerous methods and devices have attempted to address the eye's failure to accommodate. Among these are monovision techniques in which a single vision lens for correction of distance vision is used in the lens wearer's dominant eye, and a single vision lens for correction of near vision is used in the non-dominant eye. Monovision is disadvantageous because it results in a loss of stereopsis. Another known method for correction of presbyopia involves the use of bifocal or multifocal contact lenses in both eyes. This approach utilizes what are sometimes referred to as simultaneous-vision (or simultaneous-image) lenses in which the power varies, typically with rotational symmetry about the lens center either smoothly, in a continuous multifocal surface, or discontinuously in a zone multifocal surface. Simultaneous-vision bifocal or multifocal lenses, however, can produce a reduction of image contrast and resolution compared to monovision. Yet another method of treating presbyopia, referred to as modified monovision, involves placing a bifocal or multifocal lens in one eye and a single-vision lens in the other eye. This method suffers the disadvantage of requiring the consideration of many lenses to provide an individual with improved performance and likewise does not completely address the aforementioned deficiencies. Combinations of the above techniques, too, have been employed but have not, in at least significant portions of the population, offered the desired subjective through focus visual performance. It is hypothesized that deficits in visual performance associated with the above-noted modes of treating presbyopia owe to their reliance upon multifocality (i.e., the projection of multiple simultaneous images onto the retina), which does not conform to natural human visual experience. In other words, by their design, bifocal and other multifocal lenses may upset natural physiologic binocular vision by allowing for multiple foci, thus producing an image that is variously focused and defocused within a single eye. And since human perceptual mechanisms are highly adaptive over a range of time scales, the wearer must go through a period of neuroadaptation before ultimately deciding whether the vision quality is acceptable.

Still other approaches have been attempted to counteract presbyopia using electroactive devices, such as those employing a variable-aperture mechanism. Reducing the aperture in the optic region of a lens is known to mitigate the effects of presbyopia to a degree by increasing the wearer's depth of focus. This effect has been attempted in electroactive ophthalmic devices that employ electronics integral with the lens to control a static or dynamic apodization mask. In such devices, the apodization mask includes an aperture mechanism not unlike a camera lens to effect a change in the wearer's depth of field. This and similar techniques primarily reliant on an aperture effect present several challenges. For example, the substantial amount of light that must be blocked to increase the depth of field with a narrowed aperture may impede the wearer's vision in certain conditions. Another disadvantage of approaches that rely on increased depth of focus is that they do not correct for optical defects of the eye as effectively as multifocal, bifocal, and other corrective lens designs. Thus, there remains a need for ophthalmic devices, methods, and apparatuses to improve the visual experience for the effective treatment of presbyopia.

Furthermore, with the increasing miniaturization of electronic devices, wearable or embeddable microelectronic devices are finding more practical uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having electronic components capable of augmenting or enhancing the performance of the eye. In another example, either with or without adjustable focus, a wearable contact lens may incorporate electronic sensors to detect concentrations of particular chemicals in the precorneal (tear) film. The use of embedded electronics in a lens assembly introduces a potential requirement for communication with the electronics, for a method of powering and/or re-energizing the electronics including power control or power management circuitry, for interconnecting the electronics, for internal and external sensing and/or monitoring, and for control of the electronics and the overall function of the lens.

Conventional contact lenses are polymeric structures with specific shapes to correct various vision problems. To achieve enhanced functionality, various circuits and components may require integration into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality. Electronic and/or powered contract lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low-light conditions. The properly designed electronics and/or arrangement of electronics on lenses may allow for projecting an image onto the retina, for example, without a variable-focus optic lens, display images and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to monitor blood sugar levels by analyzing components of the tear film without the need for drawing blood. In addition, an appropriately configured lens may incorporate sensors for monitoring cholesterol, sodium, and potassium levels, as well as other biological markers. This, coupled with a wireless data transmitter, could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The proper combination of devices could yield potentially unprecedented functionality; however, there are a number of difficulties associated with the incorporation of extra components in an optical-grade polymer ophthalmic lens. In general, it is difficult to manufacture such components directly on the lens because of the small scale and complex shape of the lens. The components may require placement on or in the lens in an extremely limited space, often with 1.5 square centimeters of transparent polymer, while protecting the components from the liquid environment on the eye. A contact lens must be comfortable and safe for the wearer even with the added thickness of additional components.

Given the area and volume constraints of an ophthalmic device such as a contact lens, and the environment in which it is to be utilized, the physical realization of the device must overcome many problems, including mounting and interconnecting a number of electronic components on a non-planar surface, the bulk of which may include optical plastic. Accordingly, there exists a need for providing a mechanically and electrically robust electronic contact lens.

II. SUMMARY OF THE INVENTION

Dynamically tunable apodized multiple-focus ophthalmic devices and methods of the present invention overcome disadvantages associated with the prior art as briefly set forth above.

In at least one embodiment, the present invention is directed toward a lens includes optical zones each having an optical power optimized for one or more focal length, a tunable apodization mask positioned within at least a portion of at least one of the plurality of optical zones, and a processor configured to vary an optical transmission characteristic of the tunable apodization mask in response to a change in a desired focal length for the wearer. In some embodiments, the tunable apodization mask includes an electrochromic material, liquid crystal material, thermochromic material, photochromic material, nanostructure material, nanoparticle material, nanocrystal material, and/or suspended particles.

In some embodiments, the variation in the optical transmission characteristic comprises a change in an opacity of the tunable apodization mask. The lens may have one or more of a zone multifocal surface, bifocal surface, and a continuous multifocal surface. And, in some embodiments, the tunable apodization mask is disposed within an encapsulated insert. In some embodiments, the tunable apodization mask includes an electrochromic device having an inner conductive layer and an outer conductive layer; a first ion transport group; and a second ion transport group. In certain embodiments, the first and second ion transport groups may be interposed between the inner and outer conductive layers in opposite orientations relative to the inner and outer conductive layers such that an electrical bias applied to the inner and outer conductive layers causes one of the ion transport groups to function in a transparent state and the other to function in an opaque state.

In further embodiments, the plurality of optical zones includes a near zone, distance zone, and an intermediate zone. In some embodiments, a near zone, distance zone, or intermediate zone resides in the center of the lens. The plurality of optical zones may include at least two distance zones and/or the optical zones may include at least two near zones. In yet another embodiment, the tunable apodization mask includes a first region corresponding to at least one of the plurality of optical zones having a first optical power and a second region corresponding to another the plurality of optical zones having a second optical power, wherein, upon receipt of a signal indicating a desired change in focus, the opacity of the first region increases or decreases and the opacity of the second region increases or decreases inversely to that of the first region.

In still other embodiments, the tunable apodization mask resides circumferentially outside or inside at least one of the plurality of optical zones such that the transmissivity through the at least one of the plurality of optical zones approximates that of the bulk material of the lens irrespective of the desired focal length for the wearer. In further embodiments, the tunable apodization mask is configured to permit at least 50% optical transmission through at least one of the plurality of optical zones irrespective of the desired focal length for the wearer. In certain embodiments, the tunable apodization mask comprises one or more fenestrations. In yet further embodiments, the optical zones may include one or more diameters optimized to provide improved through focus visual performance based on one or more of the wearer's ocular optical characteristics, luminance, refraction, age, and vergence pupillary response. Certain embodiments may include a rigid interconnect structure configured to create electrical connectivity between the tunable apodization mask and the processor, in which the interconnect structure is composed of a translucent material and is dimensioned to include at least one void. And, in some embodiments, the optical zones may be decentered by an amount calculated to offset, at least partially, an expected decentration of the lens on an eye of the wearer.

Yet other embodiments are directed to non-transitory computer-readable media for use in an ophthalmic device having optical zones each having an optical power optimized for one or more focal lengths, the computer-readable medium including stored instructions that when executed by a processor perform the steps of: receiving real-time focus data from one or more focus sensors; determining, based on the real-time focus data from the one or more focus sensors, a desired focal length of the wearer; and actuating a tunable apodization mask positioned within at least a portion of the at least one of the plurality of optical zones; wherein actuating the tunable apodization mask apodizes light passing through at least one of the optical zones that is not optimized for the desired focal length of the wearer. In some embodiments, determining whether a change of focus is required includes comparing a mode associated with the data to a current mode of the tunable apodization mask. And in still further embodiments, a current mode of the tunable apodization mask includes a near-vision mode, a distance-vision mode, and/or an intermediate-vision mode.

III. BRIEF DESCRIPTION OF THE DRAWINGS

The foregoing and other features and advantages of the invention will be apparent from the following, more particular description of preferred embodiments of the invention, as illustrated in the accompanying drawings.

FIGS. 10A and 10B illustrate general operating principles of an exemplary embodiment.

IV. DETAILED DESCRIPTION

Glossary

Figure 1:
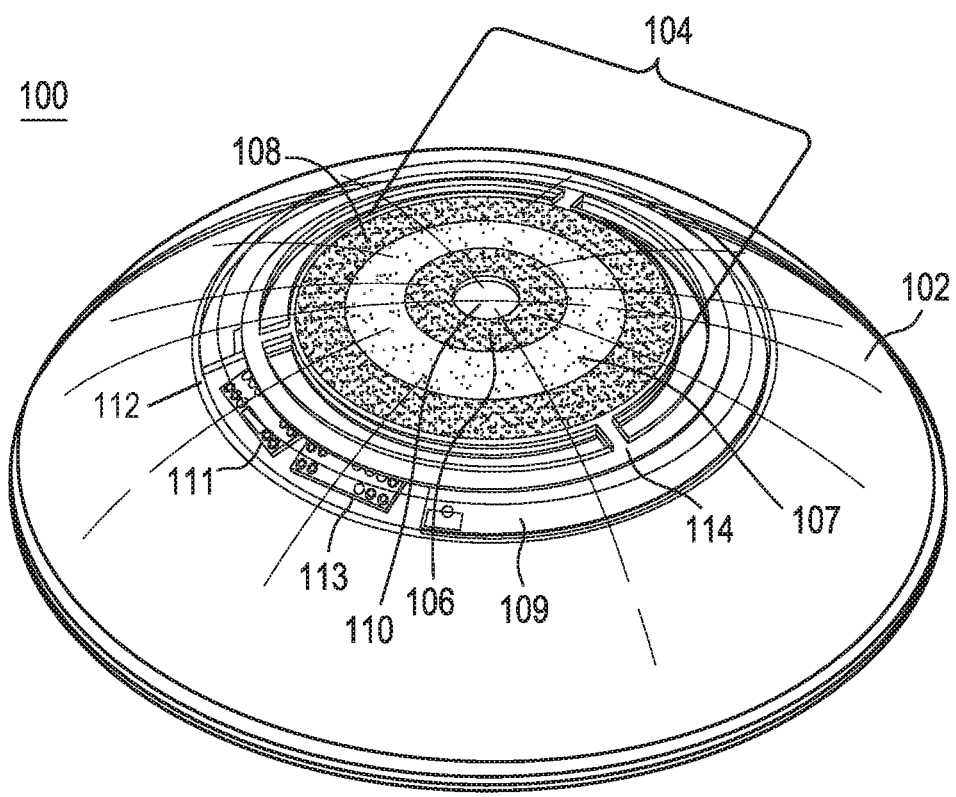
FIG. 1 illustrates an exemplary tunable apodized multiple-focus powered contact lens in accordance with an embodiment of the present invention.

With respect to the terms used in this disclosure, the following definitions are provided. The polymer definitions are consistent with those disclosed in the Compendium of Polymer Terminology and Nomenclature, IUPAC Recommendations 2008, edited by: Richard G. Jones, Jaroslav Kahovec, Robert Stepto, Edward S. Wilks, Michael Hess, Tatsuki Kitayama, and W. Val Metanomski.

As used herein, the term "about" or "approximately" refers to a range of +/−5% of the number that is being modified. For example, the phrase "about 10" would include both 9.5 and 10.5.

Unless otherwise indicated, ratios, percentages, parts, and the like are by weight.

Unless otherwise indicated, numeric ranges, for instance as in "from 2 to 10," are inclusive of the numbers defining the range (e.g., 2 and 10).

The term "apodized" or "apodization" refers to a condition of being optically filtered or the effect of optical filtering, e.g., a change in opacity.

The term "multifocal" refers to a lens having more than one optical powers.

The term "bifocal" is used interchangeably with "multifocal" for the purposes of the present description.

The term "continuous multifocal," also sometimes referred to as extended depth of focus lenses, progressive lenses, graduated prescription lenses, progressive addition lenses, and/or varifocal lenses, are lenses characterized by a gradient of lens powers.

The term "zone multifocal surface" refers to a multifocal lens with regions of optical power correction meeting at relatively abrupt discontinuities as compared to a continuous multifocal surface.

The term "multiple-focus lens" refers to any lens having one or more regions of corrective optical powers and includes multifocal, bifocal, continuous multifocal, zone multifocal lenses.

The term "fenestration" refers to an area through which oxygen or other desirable liquids or gases may traverse.

The term "ion transport group" refers to an electrochromic layer, ion storage layer, and/or electrolyte layer that function together within an electrochromic device.

The term "biomedical device" refers to any article that is designed to be used while either in or on mammalian tissues or fluids, and preferably in or on human tissue or fluids. Examples of these devices include but are not limited to wound dressings, sealants, tissue fillers, drug delivery systems, coatings, adhesion prevention barriers, catheters, implants, stents, and ophthalmic devices such as intraocular lenses and contact lenses. The biomedical devices may be ophthalmic devices, particularly contact lenses, most particularly contact lenses made from silicone hydrogels or conventional hydrogels.

The term "ocular surface" includes the surface and glandular epithelia of the cornea, conjunctiva, lacrimal gland, accessory lacrimal glands, nasolacrimal duct and meibomian gland, and their apical and basal matrices, puncta and adjacent or related structures, including eyelids linked as a functional system by both continuity of epithelia, by innervation, and the endocrine and immune systems.

The term "ophthalmic device" refers to any device which resides in or on the eye or any part of the eye, including the ocular surface. These devices can provide optical correction, cosmetic enhancement, vision enhancement, therapeutic benefit (for example as bandages) or delivery of active components such as pharmaceutical and nutraceutical components, or a combination of any of the foregoing. Examples of ophthalmic devices include but are not limited to lenses, optical and ocular inserts, including but not limited to punctal plugs, and the like. "Lenses" include soft contact lenses, hard contact lenses, hybrid contact lenses, intraocular lenses, and inlay or overlay lenses. The ophthalmic device may comprise a contact lens.

The term "contact lens" refers to an ophthalmic device that can be placed on the cornea of an individual's eye. The contact lens may provide corrective, cosmetic, or therapeutic benefit, including wound healing, the delivery of drugs or nutraceuticals, diagnostic evaluation or monitoring, ultra-violet light blocking, visible light or glare reduction, or any combination thereof. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

The biomedical devices, ophthalmic devices, and lenses of the present invention may be comprised of silicone hydrogels or conventional hydrogels. Silicone hydrogels typically contain at least one hydrophilic monomer and at least one silicone-containing component that are covalently bound to one another in the cured device.

The term "optical zone" or "optic zone" refers to an area of a lens through which light passes from an object before entering a wearer's retina.

The term "polymerizable compound" means a compound containing one or more polymerizable groups. The term encompasses, for instance, monomers, macromere, oligomers, prepolymers, cross-linkers, and the like.

"Polymerizable groups" are groups that can undergo chain growth polymerization, such as free radical or cationic reactive groups. Non-limiting examples of polymerizable groups include acrylate, methacrylate, styryl, vinyl, allyl, N-vinyl lactam, and the like.]

A "silicone-containing component" is a monomer, macromer, prepolymer, cross-linker, initiator, additive, or polymer in the reactive mixture with at least one silicon-oxygen bond, typically in the form of siloxy groups, siloxane groups, carbosiloxane groups, and mixtures thereof.

A "polymer" is a target macromolecule composed of the repeating units of the monomers used during polymerization.

An "initiator" is a molecule that can decompose into radicals which can subsequently react with a monomer to initiate a free radical polymerization reaction. A thermal initiator decomposes at a certain rate depending on the temperature; typical examples are azo compounds such as 1,1'-azobisisobutyronitrile and 4,4'-azobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzyl, benzoin, acetophenone, benzophenone, camphorquinone, and mixtures thereof as well as various monoacyl and bisacyl phosphine oxides and combinations thereof.

A "cross-linking agent" is a di-functional or multi-functional monomer which can undergo free radical polymerization at two or more locations on the molecule, thereby creating branch points and a polymeric network. Common examples are ethylene glycol dimethacrylate, tetraethylene glycol dimethacrylate, trimethylolpropane trimethacrylate, methylene bisacrylamide, triallyl cyanurate, mixtures thereof and the like.

A "polymeric network" is a cross-linked macromolecule that can swell but cannot dissolve in solvents. "Hydrogels" are polymeric networks that swell in water or aqueous solutions, typically absorbing at least 10 weight percent water. "Silicone hydrogels" are hydrogels that are made from at least one silicone-containing component with at least one hydrophilic component. Hydrophilic components may also include non-reactive polymers.

"Conventional hydrogels" refer to polymeric networks made from components without any siloxy, siloxane or carbosiloxane groups. Conventional hydrogels are prepared from reactive mixtures comprising hydrophilic monomers. Examples include 2-hydroxyethyl methacrylate ("HEMA") homopolymers or copolymers with N-vinyl pyrrolidone ("NVP"), N, N-dimethylacrylamide ("DMA"), methacrylic acid; or polymers containing vinyl acetate. U.S. Pat. Nos. 4,436,887, 4,495,313, 4,889,664, 5,006,622, 5,039459, 5,236,969, 5,270,418, 5,298,533, 5,824,719, 6,420,453, 6,423,761, 6,767,979, 7,934,830, 8,138,290, and 8,389,597 disclose the formation of conventional hydrogels. Commercially available conventional hydrogels include, but are not limited to, etafilcon, genfilcon, hilafilcon, lenefilcon, nesofilcon, omafilcon, polymacon, and vifilcon, including all of their variants.

"Silicone hydrogels" refer to polymeric networks made from at least one hydrophilic component and at least one silicone-containing component. Examples of silicone hydrogels include acquafilcon, asmofilcon, balafilcon, comfilcon, delefilcon, enfilcon, falcon, fanfilcon, formofilcon, galyfilcon, lotrafilcon, narafilcon, riofilcon, samfilcon, senofilcon, somofilcon, and stenfilcon, including all of their variants, as well as silicone hydrogels as prepared in U.S. Pat. Nos. 4,659,782, 4,659,783, 5,244,981, 5,314,960, 5,331,067, 5,371,147, 5,998,498, 6,087,415, 5,760,100, 5,776,999, 5,789,461, 5,849,811, 5,965,631, 6,367,929, 6,822,016, 6,867,245, 6,943,203, 7,247,692, 7,249,848, 7,553,880, 7,666,921, 7,786,185, 7,956,131, 8,022,158, 8,273,802, 8,399,538, 8,470,906, 8,450,387, 8,487,058, 8,507,577, 8,637,621, 8,703,891, 8,937,110, 8,937,111, 8,940,812, 9,056,878, 9,057,821, 9,125,808, 9,140,825, 9,156,934, 9,170,349, 9,244,196, 9,244,197, 9,260,544, 9,297,928, 9,297,929 as well as WO 03/22321, WO 2008/061992, and US 2010/0048847. These patents are hereby incorporated by reference in their entireties.

The terms "reactive mixture" and "reactive monomer mixture" refer to the mixture of components (both reactive and non-reactive) which are mixed together and when subjected to polymerization conditions form the conventional or silicone hydrogels of the present invention as well as contact lenses made therefrom. The reactive monomer mixture may comprise reactive components such as the monomers, macromere, prepolymers, cross-linkers, and initiators, additives such as wetting agents, release agents, polymers, dyes, light absorbing compounds such as UV absorbers, pigments, dyes and photochromic compounds, any of which may be reactive or non-reactive but are capable of being retained within the resulting biomedical device, as well as pharmaceutical and nutraceutical compounds, and any diluents. It will be appreciated that a wide range of additives may be added based upon the biomedical device which is made and its intended use. Concentrations of components of the reactive mixture are expressed as weight percentages of all components in the reactive mixture, excluding diluent. When diluents are used, their concentrations are expressed as weight percentages based upon the amount of all components in the reactive mixture and the diluent.

"Reactive components" are the components in the reactive mixture which become part of the chemical structure of the polymeric network of the resulting hydrogel by covalent bonding, hydrogen bonding, electrostatic interactions, the formation of interpenetrating polymeric networks, or any other means.

The term "silicone hydrogel contact lens" refers to a contact lens comprising at least one silicone hydrogel. Silicone hydrogel contact lenses generally have increased oxygen permeability compared to conventional hydrogels. Silicone hydrogel contact lenses use both their water and polymer content to transmit oxygen to the eye.

"Real-time" refers not to instantaneously but rather to a period during which data may be received, processed, and acted upon without exceeding an acceptable subjective tolerance of a commercially significant population of wearers.

"Tunable" refers to the ability of a device to have one or more of its operating parameters to be modified or changed. A "dynamically" tunable device is capable of effecting a change in such an operating parameter in real time or near-real time, such as in response to a change in a physiological state or condition.

Vision correction, and potentially vision enhancement, is typically achieved in spectacle lenses, contact lenses, intraocular lenses (IOL's) and other ophthalmic devices through static optics. For example, spectacle lenses or contact lenses to treat myopia (nearsightedness) comprise lenses with spherical power to correct focus onto the retina caused by defects in the cornea, crystalline lens or eye shape. However, because these lenses are optically static, they do not match the human eye's natural response which is a variable-focus action accomplished by varying the optical power of the eye's crystalline lens. In presbyopic individuals, the eye's natural ability to accommodate with different focal lengths is greatly reduced leading to a loss of function and annoyance. Recent advancements in the field have included spectacle lenses and even IOL's with some dynamic accommodation, for example, electronic spectacle lenses or so-called accommodating IOL's to achieve a limited amount of optical power change. These existing systems are limited by only covering a small range of add power, perhaps only +1 diopter, requiring spectacle lenses to be worn, requiring surgery to implant an IOL, and other drawbacks.

Conventional contact lenses are polymeric structures with specific shapes to statically correct various vision problems as briefly set forth above. To achieve enhanced functionality, various circuits and components should be integrated into these polymeric structures. For example, control circuits, microprocessors, communication devices, power supplies, sensors, actuators, light emitting diodes, and miniature antennas may be integrated into contact lenses via custom built optoelectronic components to not only correct vision, but to enhance vision as well as provide additional functionality as is explained herein. Electronic and/or powered contact lenses may be designed to provide enhanced vision via zoom-in and zoom-out capabilities or just simply modifying the refractive capabilities of the lenses. Electronic and/or powered contact lenses may be designed to enhance the visual perception of color and resolution, to display textural information, to translate speech into captions in real time, to offer visual cues from a navigation system, to provide image processing and internet access. The lenses may be designed to allow the wearer to see in low light conditions. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium and potassium levels as well as other biological markers. This coupled with a wireless data transmitter could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

As set forth above, the present invention relates to an ophthalmic device such as a contact lens comprising many components. The proper combination of devices could yield potentially unprecedented functionality; however, there are many difficulties associated with the incorporation of extra components in optical-grade polymer that makes up the ophthalmic lens. In general, it is difficult to manufacture such components directly on the lens because of the small scale and complex shape of the lens. The components to be placed on or in the lens need to be miniaturized and integrated onto areas in the range of 1.5 square centimeters of a transparent polymer, or less in some instances, seventeen (17) square millimeters, while protecting the components from the liquid environment on the eye; A contact lens must be comfortable for the wearer even with the added thickness of additional components.

In addition to potential size constraints, electronic devices incorporated into a contact lens should be robust and safe for use in an essentially aqueous environment. Tears have a pH of about 7.4 and are about 98.2 percent water and 1.8 percent dissolved physiological salts, including electrolytes such as sodium, potassium, calcium, magnesium, and chlorides. This is a somewhat harsh environment in which to introduce electronics. Also, contact lenses are generally designed to be worn for at least four hours and preferably longer than eight hours.

Electronic components require energy. This energy may be supplied from any number of internal or external sources, such as built-in batteries. Since batteries and other potential energy sources have limited potential at these sizes, all electronic components, including the lens driver, are preferably designed to consume as little power as possible so that the contact lenses may be worn for a sufficient period of time even after sitting idle for a relatively extended period of time (shelf life). Finally, all components in an electronic contact lens must be biocompatible and safe. Accordingly, all electronics incorporated into the contact lens ideally should meet the aforementioned design parameters; namely, size, survivability in an aqueous solution, power consumption and safety.

Referring to FIG. 1, at 100 an isometric view of an exemplary tunable apodized multiple-focus powered contact lens embodiment is depicted. The device includes a lens body 102, which may be composed of any number of suitable ophthalmic materials, including a hydrogel or silicone hydrogel, as described in more detail below. The lens body 102 may surround the remainder of the components of the device. The lens body 102 is preferably formed with an optical design having one or more optical zones each having an optical power, such as a multifocal or bifocal design with dioptric powers positioned at one or more diameters relative to the center of the lens and having widths optimized to provide improved through focus visual performance based on one or more of the wearer's ocular optical characteristics, luminance, refraction, age, and vergence pupillary response. The lens may have one or a combination of multi-focus surfaces, such as a zone multifocal surface, a bifocal surface, or a continuous multifocal surface. A zone multifocal surface refers to a multifocal lens with regions of optical power correction meeting at relatively abrupt discontinuities as compared to a continuous multifocal surface, which exhibits a gradient of optical power change. The term "zone" is used to describe a region of the lens having one or a range of optical powers and may be applied equally to discussions of zone multifocal surfaces, bifocal surfaces, and/or continuous multifocal surfaces.

In the embodiment illustrated, several components are embedded in the lens body material, including a tunable apodization mask 104. The tunable apodization mask 104 may be positioned within at least a portion of the optical zones of the lens 102 so that changes (i.e., tuning) of the tunable apodization mask may selectively modify the optical transmission characteristics of light traveling through the desired optical zone. In this example, the amount of light traveling through specific annular optical zones is selectively tuned by adjusting the opacity of the tunable apodization mask. However, a host of possible optical transmission characteristics of light traveling through the optical zones via the tunable apodization mask, including but not limited to the amount, color, optical path length, and refractive index, may be varied as desired using appropriate materials in the tunable apodization mask. The materials include, but are not limited to liquid crystal material, thermochromic material, photochromic material, nanostructure material, nanoparticle material, nanocrystal material, or suspended particles and combinations. One of skill in the art may recognize and select from among these or other materials to meet the relevant design constraints and to achieve the desired modification to the optical transmission characteristics, as mentioned above.

In this example, tunable apodization mask 104 employs an electrochromic device having regions that may be electroactively switched between an opaque and transparent state in order to block amounts of light entering the eye through specified optical zones of the lens. Tunable apodization mask 104 includes regions 106 and 108 corresponding to two optical zones of the lens having focal power(s) optimized for distance vision. Likewise, mask 104 includes another region 107 that corresponds to an optical zone optimized for near vision. For the purposes of this description, a region of an apodization mask is said to correspond to an optical zone when that region is positioned in at least a portion of the particular optical zone of the ophthalmic device. Further, "optimized" as used in this disclosure, means an optical design or correction feature that enhances vision at a focal length or range of focal lengths; the term is not meant to imply the absolute best or most effective design. A central region 110 may represent an area of the lens optimized for near, distance, intermediate vision or another focal length or range of focal lengths. In clinical terms, distance vision is typically considered to be within a range of 0 to ⅙ D (infinity to 6 meters), near vision is considered 2 to 3 D (0.5 to 0.33 meters), and intermediate vision is anywhere in-between near and far vision. However, for the purposes of this disclosure, near, distance, and intermediate vision are not constrained to any particular range. The terms are used herein merely to convey relative distances and associated accommodative demands.

As in exemplary apparatus 100, the apodization mask may reside circumferentially outside of central region 110 such that the transmissivity of light through the central zone is relatively unimpeded and therefore approximates that of the bulk material of the lens irrespective of the desired focal length of the wearer. Said another way, central region 110 may be described as being non-apodized. In some cases, by leaving this central region of the lens void of the material(s) that make up the tunable apodization mask, oxygen may more freely pass through the central region of the lens to the cornea, and thus the overall oxygen permeability of the lens may be increased. This advantage may be achieved because the material(s) making up the bulk of the lens generally may be expected to have a higher oxygen permeability (Dk) than the material of the tunable apodization mask. Consequently, the electrochromic material creates a region of the lens with relatively low oxygen transmission to the underlying cornea. In these circumstances, regions surrounding the mask may compensate by incorporating material(s) that permit a relatively higher amount of oxygen to reach the ocular surface. It will be appreciated that it may be helpful for other portions of the lens likewise to be free of material associated with the tunable apodization mask to further enhance oxygen transmission to the ocular surface. In some embodiments, this may be accomplished by creating multiple fenestrations in the tunable apodization mask, as discussed in more detail below.

In this example, regions 106 and 108 of the tunable apodization mask have been shaded to illustrate a selective increase in the opacity of the tunable apodization mask consistent with the wearer's desire to focus on an object relatively near the wearer. This may be described herein as regions 106 and 108 being apodized or as functioning in an opaque "state" or "mode." Likewise, region 107, illustrated with a light fill in the figure, can be described as functioning in a transparent state. More particularly, by blocking some or all light entering the eye through the zone(s) of the lens optimized for distance, light waves entering the eye are limited to those optimized for near vision and/or intermediate vision. By reducing the additional foci associated with distance vision (i.e., where the user is not focused), while correspondingly increasing the share of visual information optimized for near vision (i.e., where the user is focused), the subjective through focus visual performance may be improved relative to traditional multifocal or bifocal lenses, while retaining the benefits of optimized vision for multiple focal lengths within a single lens.

As discussed in more detail below, the tunable apodization mask may be configured to receive a signal from the processor indicating a desired change in focus for the wearer, for example, from near to far or vice versa. Upon receipt of the signal, the opacity of the tunable apodization mask in the region(s) corresponding to near increases or decreases, and the opacity of the region(s) corresponding to far increases or decreases inversely to that of the near regions. In addition, or in lieu of, the near and far scenarios, there may be any other number of states and regions that could be configured to vary either relatively to or independently from one another. Any number of discrete or continuously variable, tunable regions may be provided depending on the optical design and multi-focus surface type of the lens. By intermittently sampling the sensors configured to detect the currently desired focal length for the wearer, the tunable apodization mask may continuously switch between states optimized for the focal length currently desired by the wearer. Likewise, some regions of the tunable apodization mask may remain static, i.e., non-apodized. For example, in some instances, it may be desirable for one or more zones to remain active whether the wearer is focusing on a subject that is near or far or somewhere in between. This may increase oxygen transmission to the cornea because these non-apodized zones may be left void, i.e., free of any corresponding portion of a tunable apodization mask, which may have a relatively low oxygen permeability compared to the rest of the lens.

Tunable apodized multiple-focus powered contact lens 100 may further include an electronic insert containing electronic components that may facilitate the operation of the ophthalmic device. The electronic insert may include a processor 111, a lens driver 113, an energy source or storage device, in this example battery 109, sensors capable of detecting the real-time desired focal length of the wearer, and electrical traces forming interconnections between these electronic components. The electrical components may be disposed on any suitable substrate such as a thinned silicon wafer. In this example, electronic insert 112 has an annular shape, with the electronic components arranged radially about the insert. Certain electronic components may also exhibit annular shapes to better conform to the annular substrate. For example, a battery 109 in this example has an annular shape that spans the radius of a significant portion of the electronic insert. Electronic insert in this embodiment is situated in the non-optical zone of the lens so as not to interfere with the vision of the wearer. However, it should be appreciated that electronics could be disposed in other regions of the lens, including the optical zone, particularly where transparent or near transparent electronics, such as transparent conducting oxides or thin film transistors, are employed or where the components are miniaturized to a degree that they do not overly impact vision. As is known in the art, refraction index matching techniques may be employed to further reduce the visibility of components residing in the optical zone of the lens. In still other embodiments within the scope of the invention, electronic components of the ophthalmic device may be arranged in other manners to maximize their density, such as by arranging electronic components on vertically stacked dies (not illustrated) or forming the electrical substrate with a three-dimensional structure, such as by a thermoforming process. It should also be noted that the electronic components and circuitry depicted herein, such as processor 111 and lens driver 113, may be combined onto single integrated circuits or separated into discrete ICs within the scope of the invention.

Figure 6:
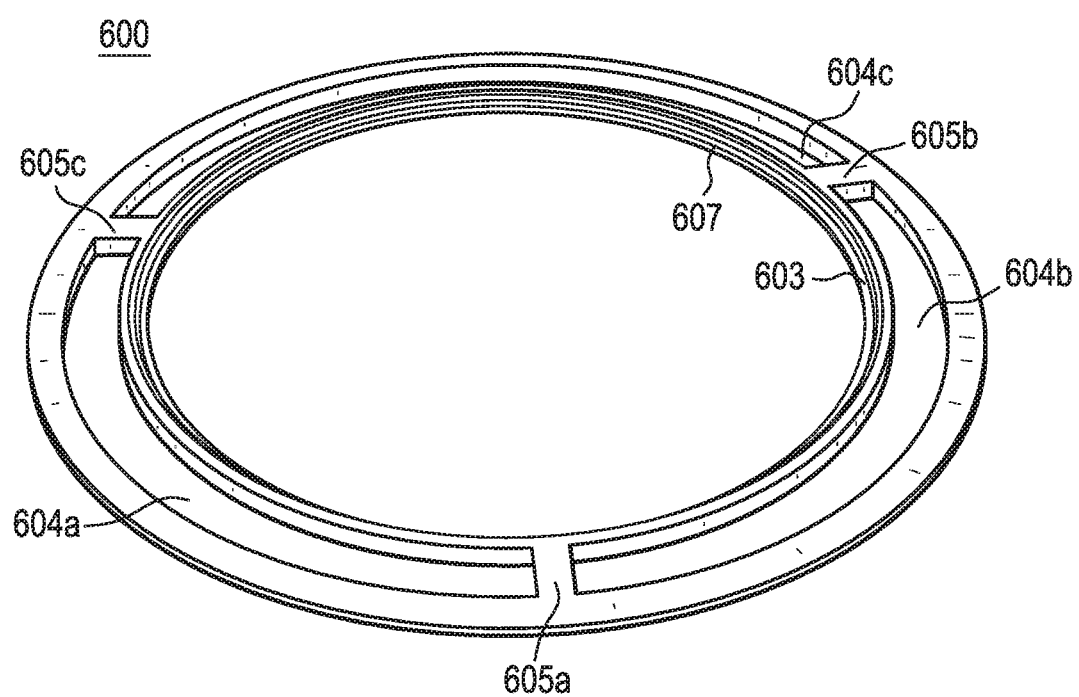
FIG. 6 illustrates an interconnect structure that may be useful in implementing some examples of the present invention.

As will be discussed further with reference to FIG. 6 below, ophthalmic devices consistent with embodiments of the present invention may include an interconnect structure that may provide electrical connectivity, support, and/or increased oxygen permeability to the device. Referring still to the tunable apodized multiple-focus powered contact lens 100 of FIG. 1, an exemplary interconnect structure 114 is shown interposed between tunable apodization mask 104 and electronic insert. An interconnect structure may, in some embodiments, serve multiple purposes, including providing electrical connectivity between one or more electronic components, e.g., processor 111, lens driver 113, and tunable apodization mask 104. Electrical traces may be embedded in or routed upon interconnect structure 114 to form interconnections at one or more electrical contacts of the electronic insert and tunable apodization mask.

Figure 2:
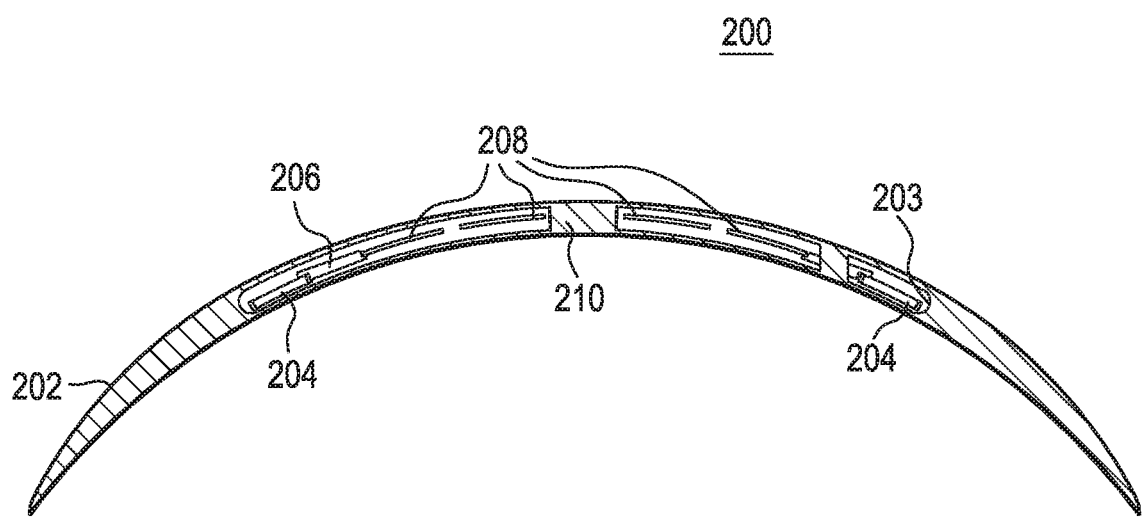
FIG. 2 illustrates a cross section of an exemplary tunable apodized multiple-focus powered contact lens in accordance with an embodiment of the present invention.

Turning now to FIG. 2, a cross section of an exemplary tunable apodized multiple-focus powered contact lens in accordance with the embodiment of FIG. 1 is provided. Lens body 202 may surround the remainder of the components of the device, as illustrated. While not necessary in all embodiments of the invention, internal components in this example, including electronic insert 204, interconnect structure 206, and tunable apodization mask 208, are disposed within an encapsulated insert defined by the boundary indicated at item 203. Encapsulating the components within an insert may provide structural rigidity, ease of manufacturing, and shielding of internal components from the aqueous monomer mixture that may be polymerized to form the lens body or from the ophthalmic environment. Encapsulation likewise may protect the wearer by preventing the ocular tissue or fluids from making contact with electronics and/or any materials of the ophthalmic device that may not be biocompatible. Any number of encapsulants may be used. However, preferable materials may be relatively transparent and shrink resistant; although none of these attributes is necessary to all embodiments of the invention. It may also be beneficial for the encapsulant to have an index of refraction similar to the lens material to minimize any potential obstruction to the vision of the wearer. Suitable materials include, for example, EPO-TEK OG603 epoxy, which has an approximate cured hardness of 84D and an index of refraction of 1.5 Nd.

Beginning at the outer periphery and moving toward the center of encapsulated insert 203, reference is first made to electronic insert 204. Electronic insert 204, in this example, contains a substrate onto which are mounted various electronic components that may facilitate the operation of the device (though not discernable from this cross section), for example, a processor, an energy source, and sensors capable of detecting a desired focal length of the wearer. It is noted that, due to the annular arrangement of the components in the embodiment depicted, the components discussed on the left side of the insert are mirrored on the right side of the insert, as indicated by the duplicate reference numerals. Moving inward, next is shown interconnect structure 206, which is interposed between tunable apodization mask 208 and electronic insert 204. The components housed within the insert may be secured to one another using an adhesive, preferably a conductive adhesive. Furthermore, as illustrated, the components may have a notch, tongue/groove, shelf, or other matingly engageable surface relative to a neighboring component to allow a precise fit within the chamber of the insert. An adhesive may be applied to one or both of the engageable surfaces to allow an adequate bonding interface between the components. Likewise, as shown in this example, the components may be oriented at angle(s) in space within the chamber of the insert so that, when interconnected with one another, the components generally track the curvature of the lens body to aid in the components' fitment within the lens body and reduce the overall lens thickness necessary to house the components. However, it should be noted that in other embodiments not illustrated herein the components may rest on a horizontal, vertical, or other plane(s) depending on the desired architecture, design, and volume constraints of the ophthalmic device.

Moving inward from interconnect structure 206 is tunable apodization mask 208, which, in this example, is physically attached to interconnect structure 206 at an overlapping lip junction. Regions 208 of the tunable apodization mask define regions that correspond to optical zones of the anterior surface lens material above regions 208 in this figure. As noted previously, by blocking some or all light entering the eye through the zone(s) of the lens optimized for distance, the light waves entering the eye are limited to those optimized for near vision and/or intermediate vision in this example. A central area of the lens 210 in this example is left void of material other than that of the lens body. For example, apodization mask 208 here resides circumferentially outside of central zone 210 such that the transmissivity of light through the central zone is unimpeded and therefore approximates that of the bulk material of the lens irrespective of the desired focal length of the wearer. By leaving this central region of the lens void of the material(s) that make up the tunable apodization mask, oxygen may more freely pass through the central region of the lens to the ocular surface, and thus the overall oxygen permeability of the lens may be increased. The central zone 210 may represent an area of the lens design optimized for near, distance, intermediate vision or another focal length or range of focal lengths.

Figure 3:
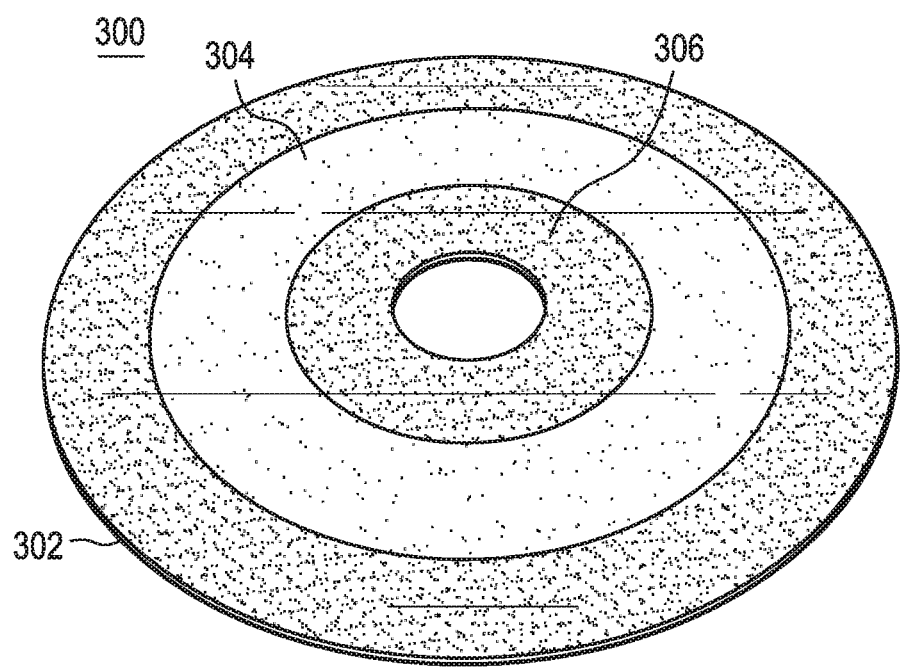
FIG. 3 illustrates an exemplary tunable apodization mask having multiple regions in which the opacity of the material may be varied.

At FIG. 3, an exemplary tunable apodization mask 300 is depicted in more detail. Electrochromic device 300 in this example includes the regions discussed above in reference to FIGS. 1 and 2. Regions 302 and 306 correspond to optical zones of the anterior surface lens material optimized for distance vision. Region 304 corresponds to an optical zone optimized for near vision. Regions 302 and 306 are shown in an opaque state and have therefore been darkened to illustrate a selective increase in the opacity of the tunable apodization mask consistent with the wearer's desire to focus on a subject relatively near to the wearer. Again, the regions illustrated in this example are illustrative only. The number, relative scale, location, size, and shape of the tunable regions may vary in myriad ways within the scope of the present invention. Indeed, as discussed in more detail below, various optimizations in the optical design of the lens may influence the shape, size, location, and other attributes of these regions (including whether they correspond to near, distance, intermediate or other zone(s) of the lens) to achieve differing desired effects to provide improved through focus visual performance based on one or more ocular optical characteristics, luminance, refraction, age, and vergence pupillary response of a particular wearer, a cross section of the population, and/or the population at large.

Device 300 may take the form of any number of electrochromic devices (ECDs), including, but not limited to a solid state ECD in which solid inorganic or organic material may be used as an electrolyte; a laminated ECD, in which liquid gel may be used as an electrolyte; a copolymer multicolor ECD; and/or combinations thereof. As compared with other alternative tunable apodization masks, an electrochromic device may offer advantages including: relatively lower power consumption, lower cost, faster switching times, and better manufacturability. As discussed in more detail with respect to FIG. 4, such an ECD includes a mechanical substrate at its anterior and posterior surfaces. The mechanical substrate may be a glass, plastic (e.g., polyethylene terephthalate "PET"), or other preferably transparent material. Within the ECD, inner and outer conductive layers (also referred to herein as electrodes) may be situated upon the respective inner and outer mechanical substrates. At least a portion of the conductive layers, or electrodes, have electrical contact with the interconnect structure (or directly with the electronics, such as those that may be housed within an electronic insert) so that an electrical bias may be applied to the electrodes to effect a change of state between a transparent, opaque, and/or colorized states depending on the type and capabilities of the chosen ECD.

Figure 4A:
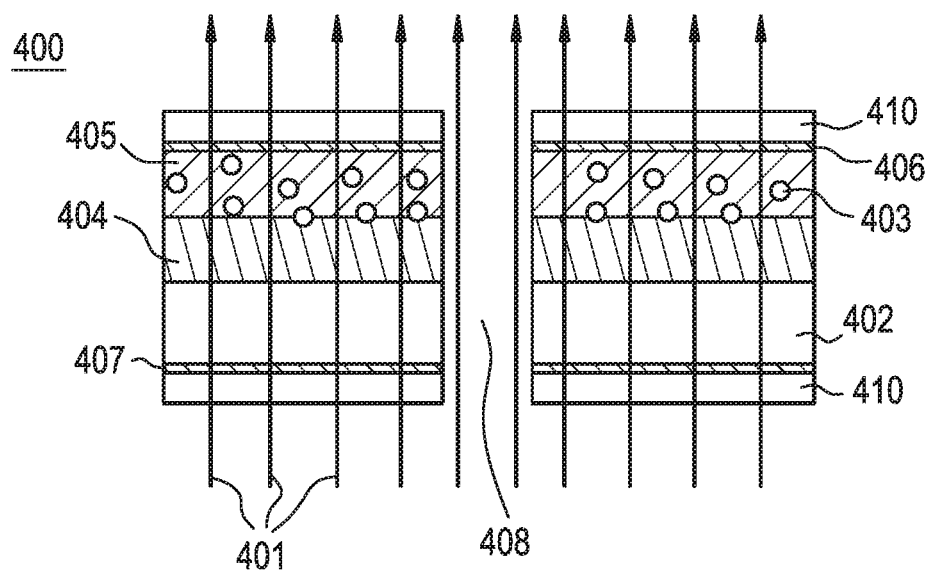
FIGS. 4A and 4B illustrate a cross section of an exemplary electrochromic device that may be used in certain embodiments of the present invention.
Figure 4B:
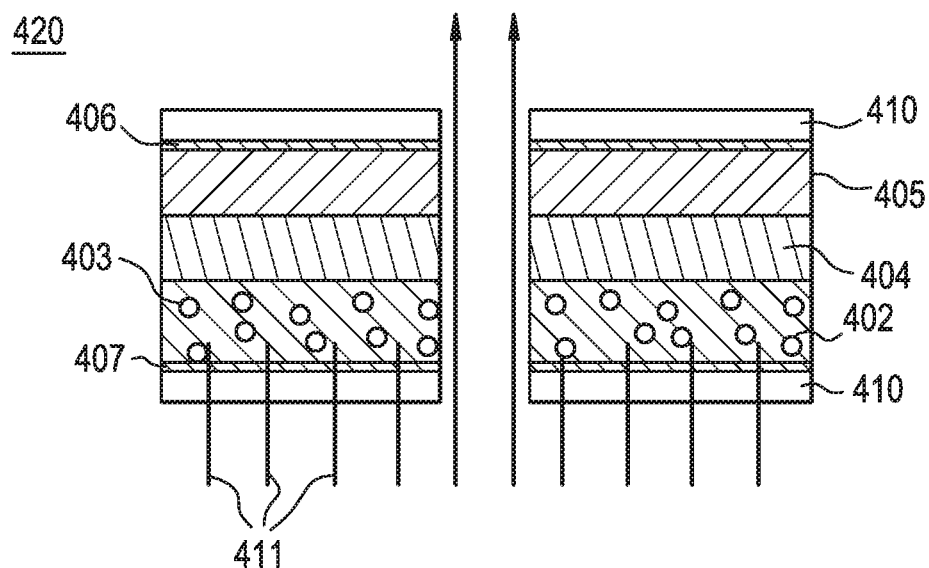

FIGS. 4A and 4B illustrate a cross section of an exemplary electrochromic device 400 that may be used in certain embodiments of the present invention. FIG. 4A illustrates the device functioning in a transparent mode whereas FIG. 4B illustrates the device functioning in an opaque mode. The basic structure of the ECD consists of an electrochromic layer 402 and an ion storage layer 405 separated by an electrolyte layer 404. An electrochromic layer, ion storage layer, and electrolyte layer that function together may be referred to collectively as an ion transport group. The electrochromic layer may be formed from electrochromic conjugated polymers (ECP) based on the benzene structure and synthesized to provide a desired wavelength absorption, process ability, and other relevant parameters. Wavelength absorption may be controlled to provide a broad range of colors. A colorless ECP may serve as the ion storage layer. Alternative electrochromic materials include metallohexacynates, viologens, transition-metal complexes, metal hydrides, among others. Chemistry of the electrolyte may vary greatly depending on the desired electrical characteristics of the electrochromic device. Various types of electrolytes may be employed including, but not limited to, liquid, gel, and dry polymers. A device with a liquid electrolyte may require a mechanical seal, while a device with a dry polymer may not require a seal. ECD 400 may be contained by a mechanical substrate layer 410 situated at the anterior and posterior surfaces of the device. The mechanical substrate may be a glass, plastic, or other preferably transparent material.

The ECD generally operates by supplying an external voltage upon electrodes 406 and 407, also referred to herein as conducting layers between which electrochromic layer 402, electrolyte 404, and ion storage layer 405 are sandwiched. The electrodes are preferably made from a transparent conductor such as indium tin oxide (i.e., ITO), but other materials may be used including monolayer graphene, graphene oxide, Graphene-Hexagonal Boron Nitride (hBN), metal nanowires, or conducting polymers. The colorization or opacity of the electrochromic material results from changing the potential of the cell by applying a voltage bias to the electrodes. As noted previously, suitable ECDs may include differing types based on application requirements including device percent transmission, transition time, life cycles, shelf life, stability, power consumption. For example, a laminated ECD may comprise a liquid or gel electrolyte for faster transition times, while an unsealed ECD may comprise a solid electrolyte designed for increased state stability.

Referring to FIG. 4A, exemplary ECD 400 is illustrated functioning in a transparent mode, as indicated by light 401 passing through the ECD. In this exemplary device, a transparent mode may be achieved by decreasing (or disabling) a voltage applied to electrodes 406 and 407. In doing so, ions 403 of the electrochromic layer migrate through electrolyte layer 404 into ion storage layer 406. Because the ions' presence in the electrochromic layer yields light absorption (or reflection in the case of some materials) in electrochromic layer 404 thus making the material relatively opaque, the ions' migration away from electrochromic layer into ion storage layer 406 permits light to travel through the ECD, causing the ECD to appear relatively transparent. A central area of the lens 408 in this example is left void of material other than that of the lens body. ECD 400 here circumscribes central zone 408 such that the transmissivity of light through the central zone is unimpeded and therefore approximates that of the bulk material in both transparent and opaque modes of operation.

Turning to FIG. 4B, exemplary ECD 420 is illustrated functioning in an opaque mode, as indicated by light 411 being blocked. In this exemplary device, an opaque mode may be achieved by reversing (i.e., increasing or enabling) the polarity applied to electrodes 406 and 407. In doing so, ions 403 in ion storage layer 405 migrate back into electrochromic layer 402. The ions' presence in the electrochromic layer yields light absorption (or reflection in the case of some materials) in electrochromic layer 402 thus making the material relatively opaque. Note that the polarity of the voltage source may be configured such that the ECD requires power only to initiate a change of state, e.g., from opaque state to transparent state. Maintaining a state, shade, or opacity, depending on the choice of ECD or configuration, therefore may not require constant voltage, thus advantageously conserving energy. To better maintain the state of the ECD, it may be advantageous to periodically apply a pulse of voltage to counteract the tendency of the ions to drift back to their unbiased state. As noted above, one of skill in the art may recognize a host of suitable electrochromic materials, including, in some cases, hydrides that reflect light rather than absorb it. In some cases, thin films made of nickel-magnesium alloy may switch back and forth from a transparent to a reflective state. It should be appreciated that the polarity of the voltage applied to the ECD may be applied reverse to the manner described herein within the scope of the invention.

Figure 5A:
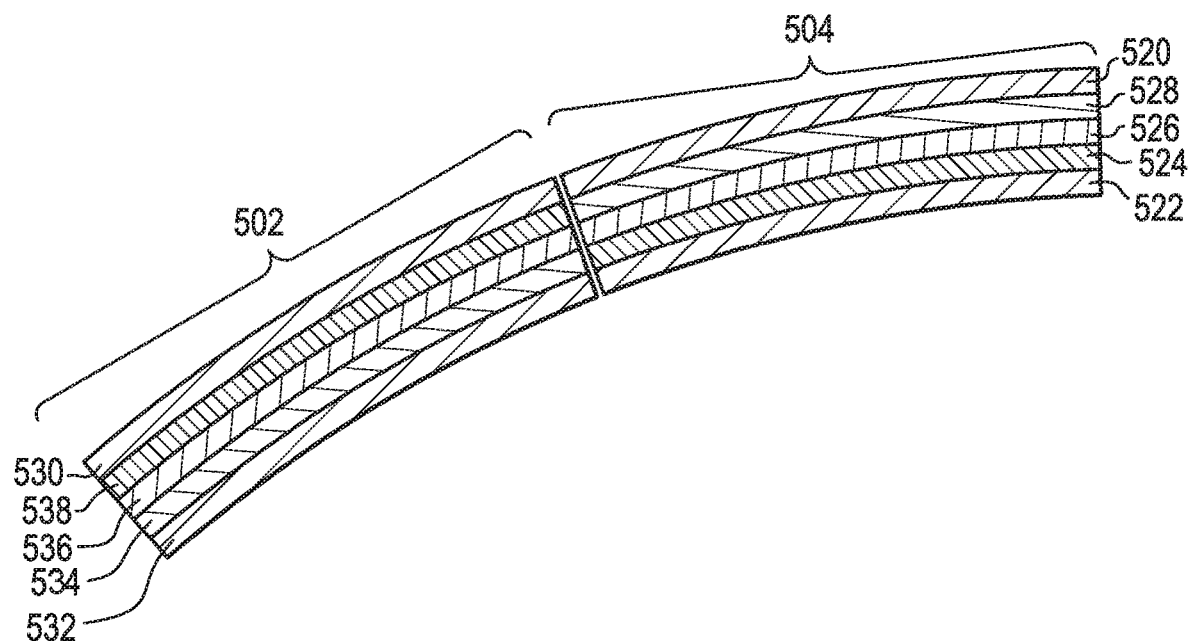
FIGS. 5A and 5B illustrate exemplary electrochromic devices that may serve as a tunable apodization mask in some embodiments of the present invention.

FIG. 5A illustrates a cross section of an exemplary tunable apodization mask having two individually sealed ECD cells. The cell 502 is made of an inner conductive layer 532 and an outer conductive layer 530. Sandwiched between these conductive layers is an ion transport group comprised of ion storage layer 538, and electrolyte layer 536, and an electrochromic layer 534. The adjacent cell making up region 504 likewise comprises of an inner conductive layer 522 and outer conductive layer 520 between which is sandwiched an ion transport group made of electrochromic layer 528, electrolyte layer 526, and ion storage layer 524. The ion transport group of this cell are oriented in reverse or opposite inner-to-outer order relative to the ion transport group of the adjacent cell. By orienting the ion transport groups of adjacent cells 502 and 504 in opposite relative configurations, a single electrical potential simultaneously applied to both cells may cause them to operate in opposing modes, i.e., one being opaque and the other transparent or vice versa. The cells in this example are individually sealed, which may be accomplished using laser welding, ultrasonic welding, or by any suitable adhesive.

Figure 5B:
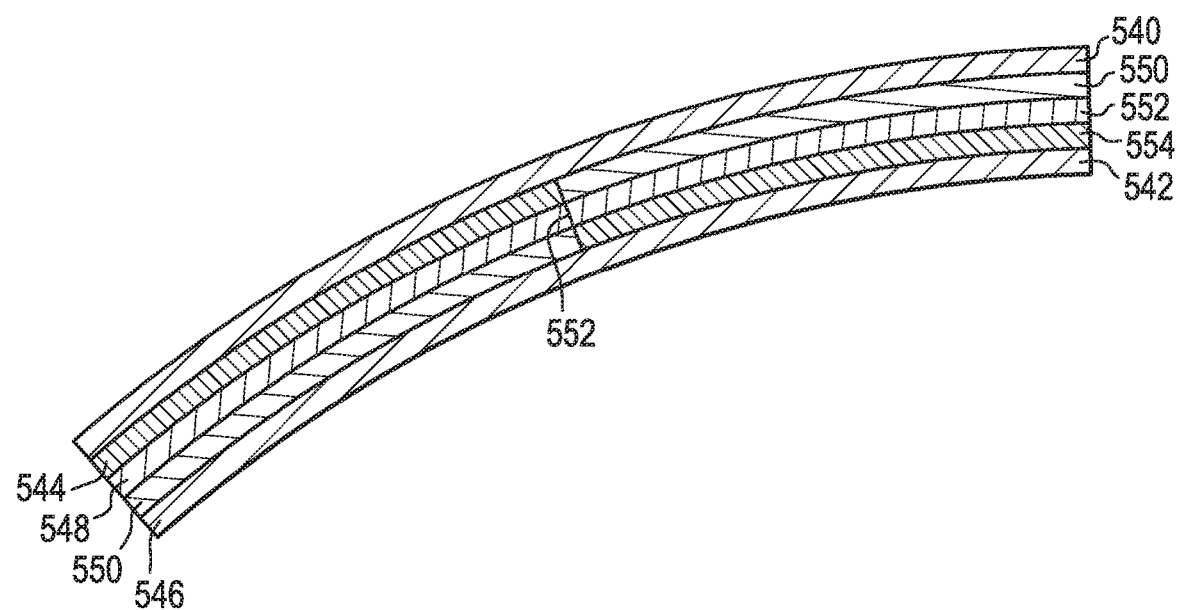

In one alternative design approach, FIG. 5B illustrates a cross section of a tunable apodization mask employing alternating layers within a single ECD cell. Here a pair of inner and outer conductive layers, 540 and 542, together contain two adjacent ion transport groups oriented opposite to each other. The ion transport groups may be applied to the inner and outer conductive materials using spray coating, conformal coating, or atomic layer deposition. The chosen conductive material may be applied by spraying the material onto the relevant surface to create ionic layers. As described above with respect to FIG. 5A, because ion transport groups of adjacent regions are in opposite relative configurations, a single electrical potential simultaneously applied to both cells will cause them to operate in opposing modes. However, by incorporating the layered ion transport groups within a single cell, fabrication of the ECD may be simplified given that fewer electrical contact points are required. In addition, control of the cell may be simplified and mechanisms for improving oxygen transport discussed elsewhere herein may be improved. The exemplary ECD designs discussed with reference to FIGS. 5A and 5B may be particularly useful in embodiments of the invention that make use of a binary or tri-state configuration, i.e., where the lens is configured to switch between near and distance modes or among near, distance, and intermediate modes where the intermediate mode is achieved by allowing light to enter distance and near zones of the lens. In these scenarios, upon receiving a signal (from a processor and/or focus sensor) indicating a desired change in focus for the wearer, the opacity of the first region of the tunable apodization mask may be configured to simultaneously increase or decrease the opacity of the near-vision zone(s) inversely to the opacity of the distance-vision zone(s).

Ophthalmic devices consistent with embodiments of the present invention may include an interconnect structure that provides electrical connectivity, support, and/or increased oxygen permeability to the device. FIG. 6 illustrates in more detail the exemplary interconnect structure 600 of the form discussed briefly above with in reference to FIG. 1. Such an interconnect structure may serve multiple purposes, including providing electrical connectivity between one or more electronic components, e.g., a processor, a lens driver, and a tunable apodization mask. Interconnect structure 600 may be formed from numerous suitable materials including but not limited to epoxy, molded glass, plastics such as Poly (methyl methacrylate)(PMMA), rigid glass permeable material, or any other clear rigid material. As will be recognized, preferable materials may be relatively transparent, shrink resistant, and rigid; although none of these attributes is necessary to all embodiments of the invention. It may also be generally beneficial for an interconnect structure to have an index of refraction similar to the lens material to minimize any potential obstruction to the vision of the wearer. Suitable materials include, for example, EPO-TEK OG603 epoxy, which has an approximate cured hardness of 84D and an index of refraction of 1.5037 Nd.

In this embodiment, interconnect structure 600 is formed of a single piece of material, though multi-piece construction is possible in certain embodiments. Exemplary structure 600 bears an annular shape dimensioned to circumscribe the outer circumference of a tunable apodization mask and to sit between an electronic insert and the tunable apodization mask. One or more void regions such as 604a, 604b, and 604c may be formed in the interconnect structure 600 in the region between the tunable apodization mask and the electronic insert. This arrangement may advantageously increase oxygen transmission to the ocular surface while maintaining electrical connectivity between the electronic insert, which may reside in the peripheral, or non-optic zone, and the tunable apodization mask situated in the central or optic zone. One or more bridge members such as 605a, 605b, and 605c, may function as substrate upon or within which electrical traces may carry electrical signals, such as the voltages used to actuate the tunable apodization mask. Electrical trace materials may include any number of suitable materials, including Au, ITO, metal nanowires, conducting polymers, or the like. Further, an internal ring surface 607 may have one or more notches or grooves upon which adhesive may be applied to form a bond with the corresponding matingly engageable surfaces of the tunable apodization mask. In some embodiments, a conductive adhesive may be applied to this region so to form electrical connections with electrode(s) of the tunable apodization mask.

Figure 7:
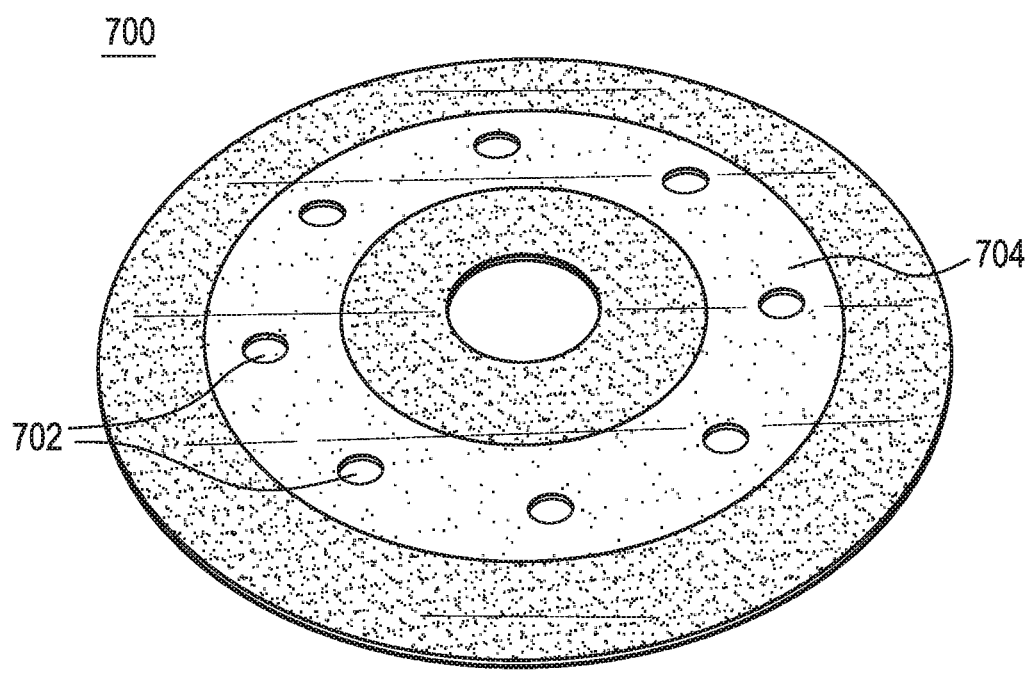
FIG. 7 illustrates a tunable apodization mask having fenestrations that may be useful for increasing the oxygen permeability of the ophthalmic device.

In some embodiments of the invention, it may be desirable to further enhance oxygen transport through the ophthalmic device by eliminating unnecessary materials from the device. This advantage may be achieved because the material(s) making up the bulk of the lens generally may be expected to have a higher oxygen permeability (Dk) than the material of other elements of the ophthalmic device, including but not limited to the electronic insert and tunable apodization mask. In some embodiments, the reduction of low-Dk material may be accomplished via fenestrations, also referred to herein as voids, or holes, or penetrations in one or more materials of the device. To illustrate one example, FIG. 7 depicts a tunable apodization mask 700 having several fenestrations that may be useful for increasing the oxygen permeability of the ophthalmic device. In this embodiment, eight circular fenestrations 702 have been created in region 704 of tunable apodization mask, which may be optimized for near vision. However, the number, size, shape, and placement of fenestrations may vary in myriad ways within the scope of the invention depending on numerous factors, including the design and layout of the regions of the apodization mask and/or the desired tradeoff between visual acuity and oxygen permeability. For example, a larger number of microfenestrations having smaller diameters and covering a larger surface area of the apodization mask than that depicted in this exemplary embodiment may have a greater efficacy with respect to ocular health. The fenestrations may be voids "filled" with air, or may be filled with an appropriate material, include silicone elastomers, silicone hydrogels and in some embodiments conventional hydrogels. In some embodiments silicone elastomers and silicone hydrogels, particularly those having an oxygen permeability of at least about 100 barrers, and in some embodiments at least about 150 barrers are desirable.

In some embodiments of the present invention, decentration may be an expected design challenge given the additional mass created by the various components discussed herein. Decentration may be of particular concern in contact lens embodiments where the lens generally floats upon the tear film of the eye and is thus subject to the effects of external forces. For example, under the force of gravity, a lens may decenter by an amount sufficient to compromise the performance of the lens due to the optical zones of the subject lens design shifting from the physiological center of the pupil. This effect may be offset in some cases by decentering one or more optical zones of the lens by an amount calculated to offset, at least partially, an expected decentration of the lens on an eye of the wearer. In the case of lens designs comprising concentric annular optical zones, this may be accomplished by configuring the lens design such that optical zones do not circumscribe the geometric center but rather the expected center point when the lens is subject to the expected effects of decentration when worn on-eye. In some embodiments, it may also be beneficial to couple this approach with features or structures that provide stabilization or anti-rotation effects, several of which are well-known in the art, including ballasts and dynamic stabilization/double thin zone(s). For example, lenses may utilize an accelerated stabilization design wherein thickened stability zones rest within the palpebral aperture above and below the 3 o'clock and 9 o'clock positions of the eye.

As noted above, numerous optical lens designs may be adopted within the scope of the invention such as a multifocal or bifocal design having dioptric powers positioned at one or more diameters relative to the center of the lens diameters and having widths optimized to provide improved through focus visual performance based on one or more of the wearer's ocular optical characteristics, luminance, refraction, age, and vergence pupillary response. A lens may have one or a combination of multi-focus surfaces, such as a zone multifocal surface, a bifocal surface, or a continuous multifocal surface. A zone multifocal surface refers to a multifocal lens with regions of optical power correction meeting at relatively abrupt discontinuities as compared to a continuous multifocal surface, which exhibits a gradient of optical power. As used herein, the term zone is used to describe a region of the lens having one or a range of optical powers and may be applied equally to embodiments utilizing any of zone multifocal surfaces, bifocal surfaces, continuous multifocal surfaces, and/or combinations thereof. Several exemplary zone multifocal design embodiments have been determined to exhibit advantageous visual performance characteristics when employed in conjunction with a tunable apodization mask. Certain illustrative embodiments are discussed herein without limiting the scope of the invention, which is to be defined by the claims. For example, still other embodiments will be appreciated as being within scope of the invention, including embodiments as noted above include a continuous multifocal surface with similar effects being realized by providing a number of zones of the tunable apodization mask such that a gradient of zones sufficiently mirrors the focal-length gradient present on the lens.

Each of the specific exemplary embodiments depicted herein will be described by way of a paraxial power profile in which approximate radial positions, diameters, and lens power for each annular zone of the lens are specified. Radial position and diameter are indicated in millimeters, whereas lens power is expressed in diopters. Individual zones of the lenses discussed below may be apodized using any possible type of tunable apodization mask, as discussed above, including, e.g., electrochromic material, a liquid crystal material, a thermochromic material, a photochromic material, a nanostructure material, a nanoparticle material, a nanocrystal material, and suspended particles or the like. Furthermore, the form of apodization discussed with respect to the following optical design embodiments is limited to changes in the transmissivity of light through a given zone or zones of the lens. This apodization may be accomplished by blocking light via an increase in opacity of a corresponding portion or portions of a tunable apodization mask. For ease of discussion, ideal "on" or "off" conditions of the tunable apodization mask are assumed, i.e., the tunable apodization mask will be assumed capable of transmitting 100% of light in a transparent state and 0% of light in an opaque state. In practice, however, available materials may not be capable of these performance parameters yet still may achieve the desired effects within the scope of the invention. For example, it has been observed that materials capable of transmitting only about 50% may be sufficient to achieve an effective transparent state whereas materials capable of transmitting not less than about 20% are sufficient to achieve an effective opaque state.

Figure 8A:
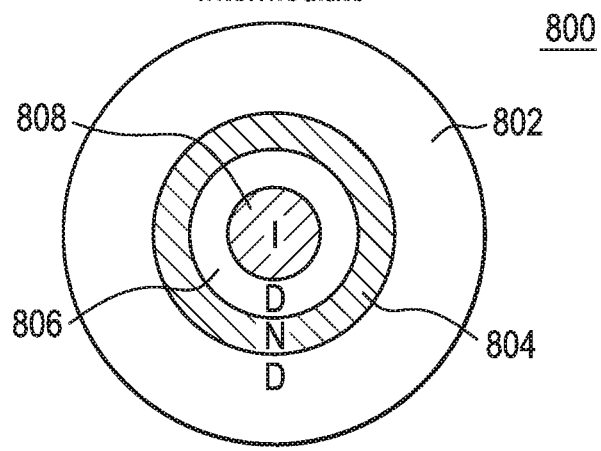
FIGS. 8A-8E represent diagrammatic illustrations of one possible multifocal lens design having four (4) optical zones each having an optical power corresponding to intermediate, near, and distance vision.
Figure 8B:
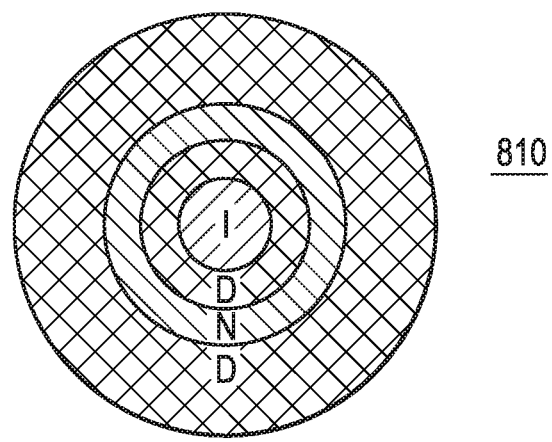
Figure 8C:
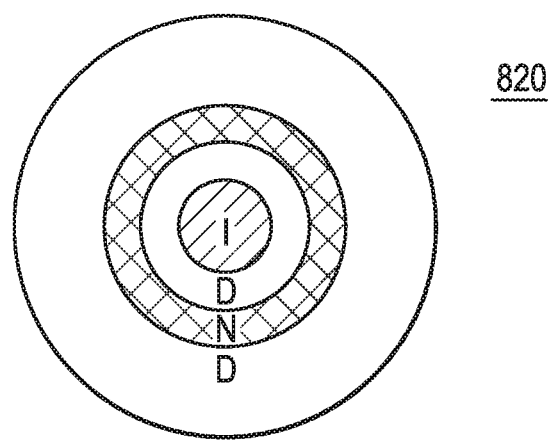

FIGS. 8A-C represent diagrammatic illustrations of one possible multifocal lens design having four (4) optical zones corresponding to intermediate-, near-, and distance-optimized vision. FIG. 8A illustrates an exemplary lens operating in intermediate-vision mode. FIG. 8B illustrates the lens operating in near-vision mode. And FIG. 8C illustrates the lens operating in distance-vision mode. For the purposes of this embodiment, distance vision may be considered a vergence demand (sometimes referred to as accommodative demand) of less than about 0.80 D (diopters). Intermediate vision may be considered within a range of about 0.80 D to 1.25 D of vergence demand. And near vision may be considered greater than about 1.25 D of vergence demand.

Beginning with FIG. 8A, a planar, two-dimensional depiction of a lens design 800 is provided from the anterior or posterior viewpoint relative to the eye. It should be noted that this depiction is for illustrative purposes and thus does not include precise scale, size, or placement of the zones. The zones in this design embodiment have a concentric, annular layout. Zones 802 and 806 have a focal power optimized for distance vision. Zone 804 has a focal power optimized for near vision. And central zone 808 has a focal power optimized for intermediate vision. As discussed with reference to previous figures, a tunable apodization mask (not discernable in this figure) includes regions corresponding to optical zones of the lens having focal power(s) optimized for one or more of zones. In this embodiment, near zone 804 and distance zones 802 and 806 correspond to regions of the tunable apodization so that the zones may be turned "on" or "off" by forcing the corresponding regions into a relatively transparent or opaque state, respectively. In this embodiment, intermediate zone 808 is static or non-apodized, meaning that it remains transparent irrespective of the desired focal length for the wearer. This may be accomplished by leaving this zone of lens void of any portion of the tunable apodization mask. In this manner oxygen permeability may be enhanced at the center of the lens.

FIG. 8A illustrates the lens functioning in intermediate-vision mode, which, in this embodiment, places all zones of the lens in an "on" or transparent state. In this mode, light travels through all zones 802, 804, 806, and 808 and regions of the tunable apodization mask corresponding to zones 802, 804, 806, and 808. FIG. 8B illustrates the same lens design embodiment functioning in a near-vision mode in which zones 802 and 806, which are optimized for distance vision, are apodized by setting corresponding regions of a tunable apodization mask to function in a relatively opaque state, thereby blocking focal lengths optimized for distance vision. Likewise, FIG. 8C illustrates the same lens design embodiment functioning in a distance-vision mode in which zone 804, which is optimized by near vision, is apodized by setting a corresponding region of a tunable apodization mask to function in a relatively opaque state, thereby blocking focal lengths optimized for near vision. In this manner, by attenuating distance conjugated zones when the wearer is focusing near, and by attenuating near conjugated zones when the wearer is focusing at distance, the subjective through focus visual performance may be improved relative to traditional multifocal or bifocal lenses, while retaining the benefits of optimized vision for multiple focal lengths within a single lens.

Figure 8D:
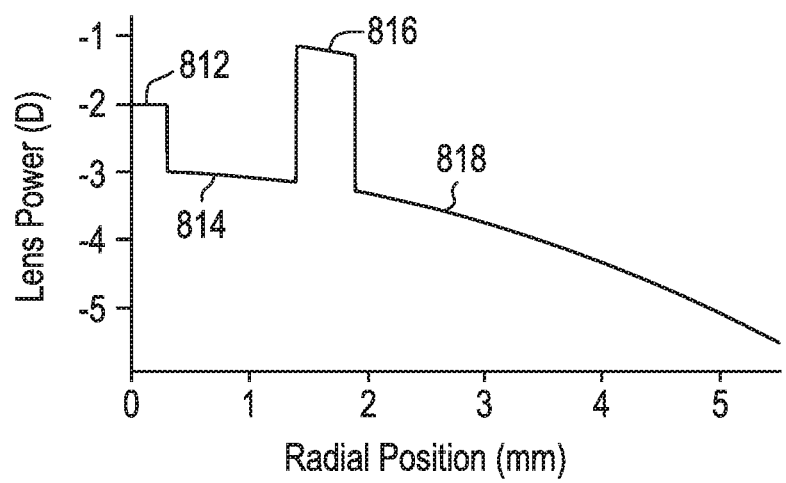

FIG. 8D presents paraxial power profile for the exemplary 4-zone, central-transmit embodiment described above with reference to FIGS. 8A-C. As used herein, a central-transmit design includes a non-apodized region in the center region of the lens. In the paraxial power profile, the X-axis represents the radial distance from the center of the lens in millimeters and the X-axis represents lens power in diopters. As reflected by the plot approaching −3D power at the center of the lens, this particular power profile is based upon a corrective lens for a patient having a refractive error of +3D. The four zones of the lens are delineated in this embodiment by abrupt discontinuities along the paraxial power profile. Beginning at the center of the lens 0 mm and extending to approximately 0.20 mm, an intermediate vision zone 812 has an approximate −2D average power. From approximately 0.20 mm and extending to approximately 1.40 mm a first distance zone 814 has a −3D power. From approximately 1.40 mm to approximately 2 mm, a near zone 816 has a −1D power. And beyond approximately 2 mm, a second distance zone 818 has a power ranging from about −3D to approximately less than −4D at the edge of the optic zone of the lens.

Figure 8E:
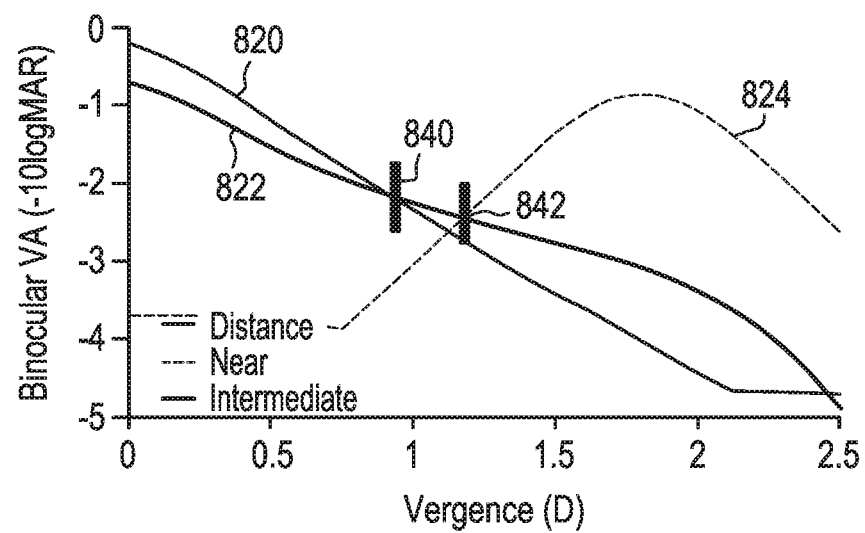

Turning to FIG. 8E, the binocular visual acuity of the lens when functioning in intermediate-, near-, and distance-vision modes. The Y-axis represents binocular visual acuity expressed in −10 log MAR (logarithm of the minimum angle of resolution), and the X-axis represents vergence expressed in diopters. A plot line is provided for each of the three modes across the full range of vergence demand to illustrate how visual acuity may vary from far to near. The plots project performance at a selected retinal luminance level of 42 cd/m^2 (candelas per square meter). Plot line 820 represents the visual acuity performance of the lens functioning in distance-vision mode, i.e., with the near zone being apodized and the distances zones being non-apodized. Plot line 822 represents the lens functioning in intermediate-vision mode, i.e., with all zones being non-apodized. And plot line 824 represents the lens functioning in near-vision mode. As expected, it may be observed that distance performance (i.e., when vergence demand is less than approximately 0.80 D, a threshold indicated by vertical break 840) is the optimal mode in this example when the lens functions in distance-vision mode. Likewise, near performance is optimal when the lens functions in near-vision mode, i.e., when vergence demand is greater than approximately 1.25 D, a threshold indicated by vertical break 842. And intermediate performance (i.e., when vergence demand is greater than approximately 0.80 D but less than approximately 1.25 D, as indicated by the region between thresholds 840 and 842) is best when the lens functions in intermediate-vision mode.

To achieve optimal performance across the range of vergence demand for a given optical design, it may be advantageous to transition between modes based on changes in vergence demand. For example, in the embodiment described with respect to FIGS. 8A-E, transitions may occur when a detected vergence demand of the wearer crosses a threshold between near and intermediate vision or intermediate and distance vision, as demarcated by vertical breaks 840 and 842. For example, where the vergence demand of the wearer exceeds threshold 842, it may be inferred that the wearer is attempting to focus on a subject relatively near, and thus the processor may be configured to cause the tunable apodization mask function in near-vision mode, if it is currently operating in a distance-vision or intermediate-vision mode. Configured in this manner in conjunction with a dynamic tunable apodization mask, the above described design exhibits improved visual acuity performance relative to commercially available multifocal contact lenses across at least a substantial portion of the vergence demand spectrum.

Figure 9A:
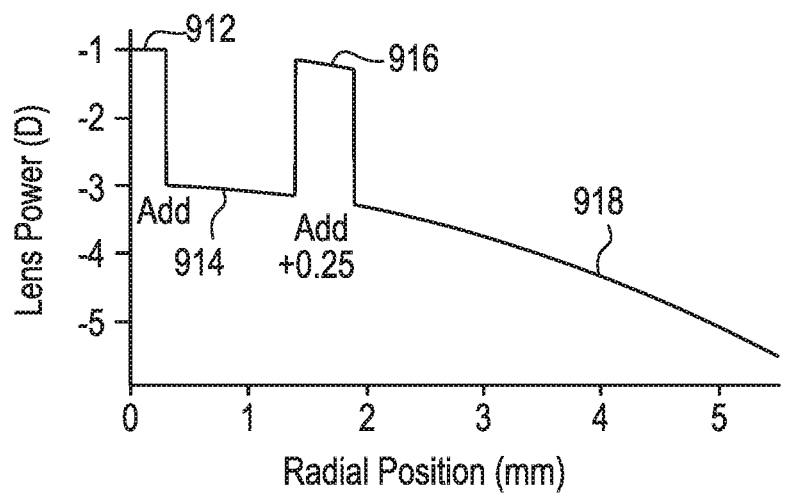
FIGS. 9A and 9B represent diagrammatic illustrations of one possible multifocal lens design having four (4) optical zones each having an optical power corresponding to intermediate, near, and distance vision and further making use of monovision techniques.

In some embodiments, subjective visual performance of a tunable apodized multiple-focus ophthalmic device in accordance with the present invention may be further improved through the application of monovision principles. By providing the wearer lenses having a differential power profiles relative to each other, the effect of binocular summation of the powers may provide added net benefit beyond that afforded by strict bifocal or multifocal designs, such as the exemplary embodiment described with reference to FIGS. 8A-8E. Turning to an monovision embodiment, FIG. 9A presents paraxial power profile for exemplary 4-zone, central-transmit design having 0.75 diopters of monovision and a 2.0 diopter add. Beginning at the center of the lens, an intermediate vision zone 912 has an approximate −1D power. Moving outward, an intermediate zone 914 has a −3D power. Next, a near zone 916 has a −1D power. And beyond approximately 2 mm, a second distance zone 918 has an average power ranging from about −3D to approximately less than −1D at the outer perimeter of the lens.

Figure 9B:
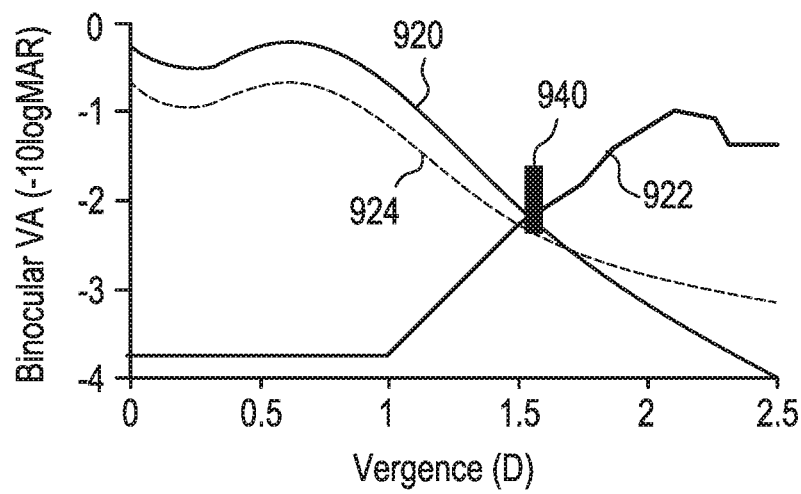

Turning to FIG. 9B, the binocular visual acuity of the lens when functioning in intermediate-, near-, and distance-vision modes. The Y-axis represents binocular visual acuity expressed in −10 log MAR (logarithm of the minimum angle of resolution), and the X-axis represents vergence expressed in diopters. A plot line is provided for each of the three modes across the full range of vergence demand to illustrate how visual acuity may vary from far to near. The plots project performance at a selected retinal luminance level of 42 cd/m^2 (candelas per square meter). A pupil diameter of 3.6 mm, 3.9 mm, and 3.4 mm are assumed for each of the distance-vision, near-vision, and intermediate-vision modes, respectively. Plot line 920 represents the visual acuity performance of the lens functioning in distance-vision mode, i.e., with the near zone being apodized and the distances zones being non-apodized. Plot line 924 represents the lens functioning in intermediate-vision mode, i.e., with all zones being nonapodized. And plot line 922 represents the lens functioning in near-vision mode. Here, it may be observed that distance performance is optimized when the lens is functioning in distance mode (i.e., when vergence demand is less than approximately 1.5 D, a threshold indicated by vertical break 940). Likewise, near performance is optimal when the lens functions in near-vision mode, i.e., when vergence demand is greater than approximately 1.5 D. Intermediate-mode performance, line 924, remains below the distance- and near-vision lines across the full range of vergence demand in this example, an optimal configuration of this particular design may not employ intermediate mode but rather rely upon direct transitions between near and distance modes when vergence demand crosses threshold 940.

Again, presented here in detail are merely two of myriad potential solutions within scope of the present invention. Generally speaking, it should be noted that increasing the number of regions and zones of a lens may yield better performance. Accordingly, an idealized solution within the scope of the present invention may involve the combination of continuous multifocal surface and continuously variable apodization mask configured in accordance with the principles outlined herein. In such embodiments, an apodization mask may include a tapered or gradient series of regions, which results in a smooth transition in the transmittance function across the corresponding optical zones thereby advantageously reducing diffractive effects such as starburst and halo. Again, myriad alternative design shapes, sizes, location, and other attributes of the tunable regions (including whether they correspond to near, distance, intermediate or other zone(s) of the lens) are possible within the scope of the invention though not specifically depicted herein, including but not limited to a design in which pie-shaped regions arranged radially about a center point on the lens in which one or more slices of the pie are optimized for near, intermediate, and distance vision.

Figure 10B:
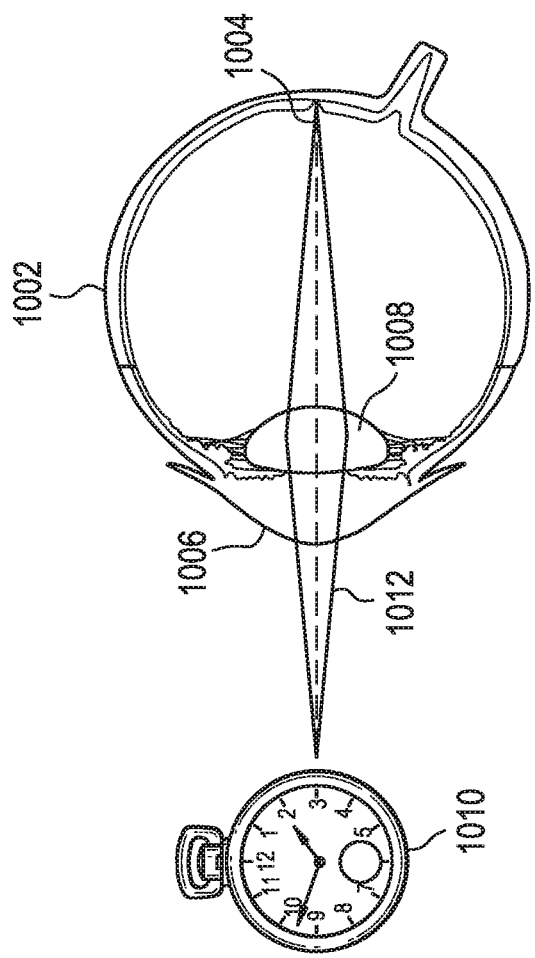
Figure 10B:
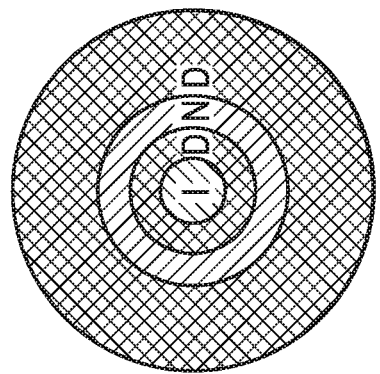
Figure 10B:
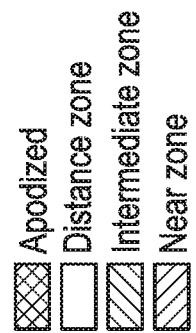

FIGS. 10A and 10B depict an eye 1002 of a patient (also referred to interchangeably as "wearer" herein) onto which an ophthalmic device of the present invention may be placed upon the surface of cornea 1006, in a contact lens embodiment; within the cornea 1006, in a corneal inlay or onlay embodiment; or within a the capsular bag 1008, in an intraocular lens embodiment. Viewing an object near a patient such as watch 1010 in FIG. 10B, triggers the eye's natural physiological response of accommodation. In a normal eye without presbyopia, accommodation adjusts the focusing power of the eye by changing the thickness of the eye's crystalline lens. By contracting ciliary muscles, the lens is caused to thicken, thereby shortening the focal length of the lens sufficiently to focus the light 1012, and thus the image of the near object sharply on the retina 1004 of the eye.

FIG. 10A illustrates an instance in which distance vision is desired for the patient so that he or she may focus on a tree 1010 in the distance. In this case, a tunable apodization mask may be configured to function in a distance-vision mode by apodizing zones optimized for near vision by causing corresponding regions of a tunable apodization mask to function in a relatively opaque state (indicated by cross hatching), thereby blocking focal lengths optimized for near vision. Likewise, FIG. 10B illustrates the same lens design embodiment functioning in a near-vision mode in which the zones optimized for distance vision is apodized by setting a corresponding region of a tunable apodization mask to function in a relatively opaque state (indicated by cross hatching). In both examples, an intermediate zone located at the center of the lens may remain nonapodized so that light transmitted through that zone approximates that of the bulk material of the lens irrespective of the desired focal length for the wearer, thereby increasing oxygen permeability and/or overall light transmission to the eye.

Ophthalmic device embodiments of the present invention may utilize one or more natural physiological responses, such as the contraction of the ciliary muscle, to trigger a change in the state of the tunable apodization mask of the invention. Other natural physiological indicators of the user's desired focal length that may function as triggers to switch between various modes of operation of the ophthalmic device include, eye gaze detection, vergence detection (divergence and/or convergence of the eyes), eye movement detection, impedance detection, and pupil diameter detection, some of which triggers are disclosed in further detail herein. Likewise, purposeful, deliberate, or conscious techniques may be used by the wearer (or third-party, such as an eye-care professional in a clinical environment) to trigger a desired change of focus, such as the use of deliberate blink or extreme-gaze patterns or a manual external device, such as a fob, smartphone, or other electronic device capable of communicating with the lens via, e.g., wireless transmission protocols. Furthermore, one or more of the aforementioned indicators or triggers may be combined, such as through the use of multi-input and voting schemes, to increase their accuracy and reduce false-positive responses. One of skill in the art will recognize the use of these natural physiological indicia or deliberate means control will require appropriate sensor(s), which may reside on an electronic insert housed within the ophthalmic device. For example, in a case where pupil diameter detection were a selected means of sensing a desired change in focal length, one or more camera(s) may be used. Eye movement detection or vergence may employ camera(s), gyroscope(s), photodiode(s) and/or accelerometer(s). It will be appreciated that further variations are possible such as the use of various sensing and detection algorithms and various modes of partitioning software and hardware among one or more integrated circuits.

Figure 11:
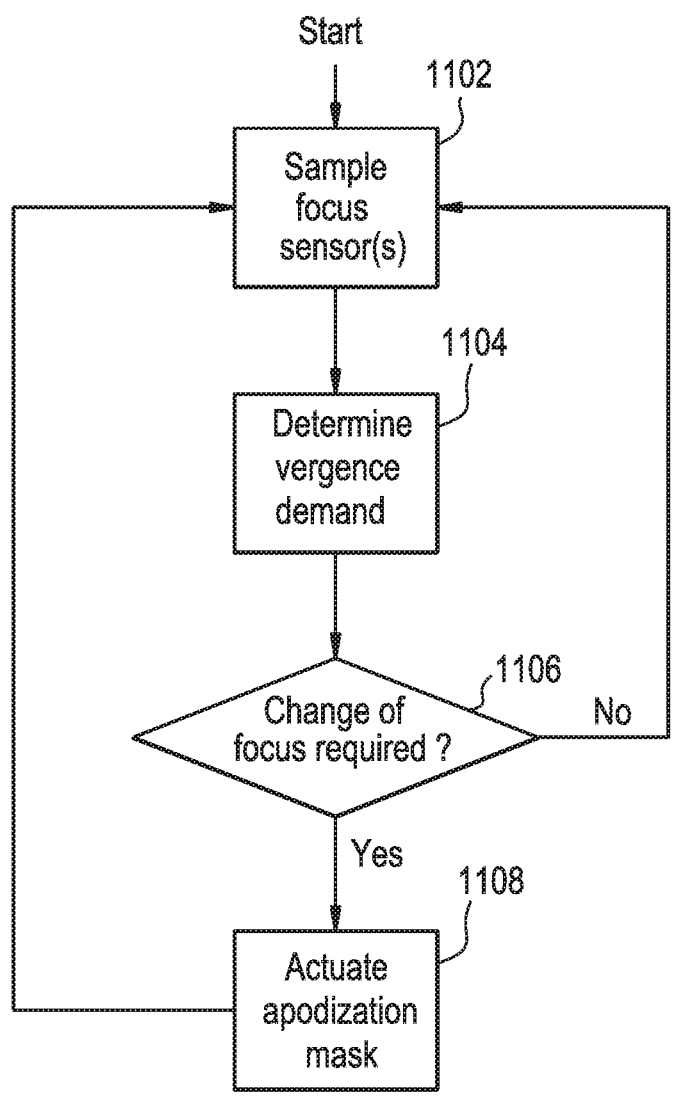
FIG. 11 illustrates an exemplary method by which an ophthalmic device within the scope of the present invention may operate.

FIG. 11 illustrates an exemplary method by which an ophthalmic device within the scope of the present invention may operate. For example, a processor may be embedded on or within an ophthalmic device and configured to execute a series of instructions stored on a computer-readable storage medium that dictate the operation of the ophthalmic device. By intermittently sampling sensors configured to detect the currently desired focal length for the wearer, a processor may cause the tunable apodization mask to switch dynamically between states optimized for the focal length desired by the wearer in real time. Vergence demand generally may be viewed as the desired focal length of the wearer, which as described elsewhere herein, may be ascertained at intermittent intervals, and, ideally, regularly enough to effect transitions between focal states that approximate the natural response and transition times of the human eye within acceptable tolerances. A sampling period of less than about 100 milliseconds and a state-change time of less than about one second are generally sufficient to meet these criteria. As will be understood by those of skill in the art, such functionality may be implemented in sequential digital logic, via state-machine logic, or by discrete digital logic, and via hardware or software. Such software or digital logic may reside in a computer-readable medium housed within the ophthalmic device, such as within an electronic insert. In one exemplary embodiment, the processor may take the form of a system controller fully integrated into a silicon CMOS integrated circuit die. However various combinations or partitions of hardware and software among one or more integrated circuits is possible as the particular design constraints dictate.

Beginning at step 1102, a processor may sample one or more focus sensors, which, as discussed above may take the form of various sensing devices, including but not limited to camera(s), gyroscope(s), photodiode(s) and/or accelerometer(s) depending on the physiological or manual trigger being monitored as an indication of the wearer's desired focal length. The ophthalmic device may employ a clocking device that drives the processor to execute steps at a frequency that satisfies power and response-time constraints. In some embodiments, a process or system controller may operate at about 850 Hz. Furthermore, multiple clock signals may drive the various components of the ophthalmic devices at differing frequencies based on the demands of the subcomponents within the domain of the respective clock. Alternatively, or in combination, a clock signal(s) may be gated to generate lower frequency clock signals for certain subcomponents, such as one or more sensors such as focus sensor(s), to further reduce power consumption. In some embodiments, focus sensor(s) may be sampled at a rate of approximately 100 Hz which may permit the ophthalmic device to effect a change of focus that approximates the natural accommodative response and/or is within a range that satisfies the subjective expectation of the wearer.

At a step 1104, the system may determine the current vergence demand of the wearer based upon real-time focus data sampled from the focus sensor(s). As used herein, vergence demand is used interchangeably with accommodative demand or desired focal length collectively to mean a measure indicative of the desired focal length of the wearer. Resolving a given sample to a corresponding vergence demand may simplify the process of determining what mode or setting (e.g., voltage level) to apply to the tunable apodization mask. As discussed herein, a lens design may have within the present invention multiple discrete zones or a continuously variable surface producing a range of differing focal powers; and a tunable apodization mask may have numerous regions and/or a continuously variable range of regions configured to apodize light incident on predetermined corresponding areas or zones of the lens. A determination of the appropriate settings to apply to a tunable apodization mask based on the data sampled from the focus sensor(s) therefore may range from simple (e.g., where there are a relatively small number of discrete optical zones and corresponding tunable regions) to complex in cases of a large number of zones or a continuous multifocal surface and/or continuously variable tunable apodization. In embodiments tending toward the former, it may be beneficial for the processor to execute an algorithm that takes as input(s) data sampled from the focus sensor(s) and generates output that may be used to actuate the tunable apodization mask to the appropriate setting, such as by setting the tunable apodization mask to a particular "mode" or by applying an appropriate voltage bias. As an alternative to an algorithmic process, such calculations may be simplified by implementing a solution using state machine logic and/or by using one or more look-up tables in which data samples and corresponding settings for the tunable apodization mask have been precalculated and stored in a computer-readable storage medium.

Moving to step 1106, the system may determine whether a change of focus is required or whether the current setting or mode of the tunable apodization mask satisfies the wearer's currently desired focal length. This determination may be made based upon the vergence demand determined at step 1104 or directly based upon data sampled from the focus sensor in step 1102 (in embodiments where step 1104 is omitted). Data obtained or generated at steps 1102 or 1104 may be compared against data representing the current mode or setting of the focus sensor(s), which may be stored as a variable, for example in a register such as an n-bit flip-flop, where n represents the number of bits needed to store the variable. If, based on a comparison of the current setting or mode with the desired setting mode, a change is not required, then the process may return to step 1102 where the focus sensor(s) may be sampled once again. However, if the comparison indicates that the current setting or mode does not meet the desired focus of the wearer, then the process continues to step 1108 where the tunable apodization mask is actuated.

At step 1108 the processor may cause the tunable apodization mask to change its mode or setting to suit the desired focal length of the wearer. For example, in discrete zone multifocal embodiments discussed herein having a near-vision, intermediate-vision, and/or distance-vision mode; the tunable apodization mask may be actuated into the mode suited to the wearer's desired focal length. Likewise, in a continuous multifocal surface having a gradient of focal powers, the tunable apodization mask may be variably tuned about the continuous surface, along a gradient of electro-chromic (or other suitable materials) or along an array of finely tuned zones. In any case, this may be accomplished by applying one or more predetermined voltage(s) to the terminals of the tunable apodization mask. The new setting for the tunable apodization mask may then be stored in a register as discussed previously for future reference. The steps of the above-described process are provided for illustrative purposes only and should not be understood as the only means of the many steps that may be used to configure the operation of a device within the scope of the invention. Furthermore, none of the steps should be considered absolute; steps may be omitted entirely, combined, and/or performed in various orders.

As an alternative or in combination with other methods discussed herein, control of a powered ophthalmic lens of the present invention may be accomplished through a manually operated external device that communicates with the lens wirelessly, such as a hand-held remote unit; this may be helpful, for example, in a clinical setting where an optometrist or ophthalmologist may seek to control the lens for testing or calibration purposes. Alternately, control of the powered ophthalmic lens may be accomplished via feedback or control signals directly from the wearer. For example, sensors built into the lens may detect blinks and/or blink patterns. Based upon the pattern or sequence of blinks, the powered ophthalmic lens may change modes.

In other embodiments of the present invention control of the powered ophthalmic lens may be enabled by an electronic system, which actuates a variable optic or any other device or devices configured to implement any number of numerous functions that may be performed. The electronic system includes one or more batteries or other power sources, power storage devices, power management circuitry, one or more sensors, clock generation circuitry, control circuitry implementing suitable control algorithms, and lens driver circuitry. The complexity of these components may vary depending on the required or desired functionality of the lens.

It is important to note that the system controller of the present invention may receive any number of inputs for controlling a powered or electronic ophthalmic lens, for example, a contact lens comprising a variable power optic element or variable-focus optic for focusing in on distant objects and focusing out on close objects.

A system controller or control system comprises one or more devices configured to manage, command, direct and/or regulate the actions of other devices and/or systems. While there are a number of different types of control systems, they generally fall into two classes or types; namely, logic or sequential control systems and feedback or linear control systems. In a logic or sequential control system, command signals are output which trigger a series of actuators in a predetermined sequence to perform one or more tasks. In a feedback control system, a control loop, including one or more sensors, control algorithms, and actuators is configured to regulate a variable at a set point or reference value. In any feedback control system, one needs to know what the system is to do, to know how well the system is performing, and to use the performance information to correct and control the system.

The components of the basic feedback control system may be described as follows. The control system comprises the system or plant to be controlled and is configured to receive an input and provide an output. The output of the plant is input to a sensor which measures one or more parameters of the plant and provides a feedback signal. The feedback signal is then subtracted, via a comparator or other suitable means, from the input signal to generate an error signal. The error signal is then input to a controller which outputs a signal to the plant thereby causing the plant to implement the desired action. Essentially, the feedback from the sensor attempts to account for all the complexities of the entire system and produces an output that is the desired result for a given input. All control systems are designed within the confines of certain control laws and typically represent tradeoffs in various aspects, including speed and accuracy. Although this description is overly simplified and described in terms of hardware, it provides the basis for feedback control systems which may be implemented in hardware, software or any combination thereof.

Feedback control systems may be further classified as proportional controllers, integral controllers, derivative controllers or combinations thereof. In a proportional controller, the control action is proportional to the error. In an integral controller, the actuating signal or input to the plant is proportional to the integral of the error. In a derivative controller, the output of the process is proportional to the rate at which the input changes. Each type of controller offers its own advantage as is known in the control art. For example, a steady state error should be achieved when utilizing an integral controller.

A sequential controller, as set forth above, is one in which a series of actions need to occur in a specific order. These actions may be quite complex, because all the conditions of the overall process must be known. Sequential controllers generally comprise logic systems to sequence commands for controlling electrical and/or mechanical actions. Programmable logic controllers and microcontrollers may be programmed for sequential control.

It will be appreciated by the skilled artisan that the system controller or subsystems associated with the system controller may incorporate features to respond to feedback provided by sensor inputs. Examples of such operations may include altering a duty cycle or power level of a subsystem in response to lower battery capacity, adjusting an internal clock frequency to synchronize to a frequency associated with received signals, and/or regulating an amount of therapeutic agent or drug delivered to the tear film of the eye in response to a measurement of tear film chemistry.

A blink detection algorithm may be a component of the system controller that detects characteristics of blinks, for example, if the lid is open or closed, the duration of the blink open or closed, the inter-blink duration, and the number of blinks in a given time period. An exemplary algorithm in accordance with the present invention relies on sampling light incident on the eye at a certain rate. Pre-determined blink patterns may be stored and compared to the recent history of incident light samples. When patterns match, the blink detection algorithm triggers activity in the system controller, for example, to activate a lens driver to change the mode of the lens.

A blink detection algorithm and associated circuitry of the present invention preferably operate over a reasonably wide range of lighting conditions and is preferably able to distinguish an intentional blink sequence from involuntary blinks. It is also preferred that minimal training is required to utilize intentional blinks to activate and/or control the powered ophthalmic lens. A blink detection algorithm and associated circuitry of the present invention provides a safe, low cost, and reliable means and method for detecting blinks via a powered or electronic contact lens, which also has a low rate of power consumption and is scalable for incorporation into an ophthalmic lens, for at least one of activating or controlling a powered or electronic ophthalmic lens.

It may be desirable to incorporate a self-contained power storage device such as, e.g., a rechargeable battery, solar cell, or capacitor. Alternately, the electronics may be inductively powered from a distance rather than being powered from a self-contained power storage device, and thus there is no need for recharging. An acceptable method for recharging a battery is through inductive coupling, whereby an external coil is magnetically coupled to a coil that is coupled to, connected to or otherwise associated with a charging circuit adapted to recharge the battery imbedded in the device.

A variety of ophthalmic devices of the invention may be prepared, including hard contact lenses, soft contact lenses, corneal onlays, corneal inlays, intraocular lenses, powered lenses, overlay lenses, or the like. Ophthalmic devices may be prepared by polymerizing a reactive mixture comprising polymerizable and non-polymerizable compounds suitable for making the desired ophthalmic device. For example, when the ophthalmic device is a contact lens, the reactive mixture may be, but is not limited to conventional hydrogels and silicone hydrogels. Thus, the reactive mixture may include one or more of: hydrophilic components, hydrophobic components, silicone-containing components, wetting agents such as polyamides, crosslinking agents, and further components such as diluents and initiators. Examples of additional suitable materials for other ophthalmic devices are known and include acrylates (rigid and foldable), hydrogels and silicones for intraocular lenses and polycarbonate for spectacle lenses.

In some embodiments, electronic components of ophthalmic devices within the scope of the present invention may be housed within an electronic insert. The ophthalmic device may be manufactured using a front curve mold part and a back curve mold part. Next, a stabilizing feature may be placed at a location between the back curve mold part and the front curve mold part, such that the stabilizing feature may orient the ophthalmic device on an eye as needed to account for considerations such as sensor location and expected decentration. The electronic insert may then be placed at a location between the back curve mold part and the front curve mold part at a predetermined position in relation to the stabilizing feature. A reactive monomer mixture may be deposited on one or both the front curve mold part and the back curve mold part before positioning the back curve mold part proximate to the front curve mold part to form a cavity in which the reactive monomer mixture, the electronic insert and the stabilizing feature may reside. The reactive monomer mixture may then be cured to form a biocompatible lens material with electronic components housed within.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic device comprising:
    a lens comprising a lens body having plurality of optical zones each having a paraxial optical power optimized to provide improved through focus visual performance;
    a tunable apodization mask positioned within at least a portion of at least one of the plurality of optical zones; and
    a processor configured to vary an opacity of the tunable apodization mask in response to a change in a desired focal length for a wearer of the ophthalmic device, wherein the varying the opacity of the tunable apodization mask selectively increases or decreases a transmissivity of light through each of the plurality of optical zones to effect a change in optical power of the ophthalmic device.

2. The ophthalmic device of claim 1, wherein the tunable apodization mask comprises at least one of an electrochromic material, a liquid crystal material, a thermochromic material, a photochromic material, a nanostructure material, a nanoparticle material, a nanocrystal material, and suspended particles.

3. The ophthalmic device of claim 1, wherein the lens has one or more of a zone multifocal surface, bifocal surface, and a continuous multifocal surface.

4. The ophthalmic device of claim 1, wherein the tunable apodization mask is disposed within an encapsulated insert.

5. The ophthalmic device of claim 1, wherein the tunable apodization mask comprises an electrochromic device comprising:
    an inner conductive layer and an outer conductive layer;
    a first ion transport group; and
    a second ion transport group;
    wherein the first and second ion transport groups are interposed between the inner and outer conductive layers in opposite orientations relative to the inner and outer conductive layers such that an electrical bias applied to the inner and outer conductive layers causes the one of the first and second ion transport groups to function in a transparent state and the other of the first and second ion transport groups to function in an opaque state.

6. The ophthalmic device of claim 1, wherein the plurality of optical zones comprises at least one of each of a near zone, distance zone, and an intermediate zone.

7. The ophthalmic device of claim 6, wherein one of the at least one near zone, distance zone, and intermediate zone resides in the center of the lens.

8. The ophthalmic device of claim 6, wherein the plurality of optical zones comprises at least two distance zones.

9. The ophthalmic device of claim 6, wherein the plurality of optical zones comprises at least two near zones.

10. The ophthalmic device of claim 6, wherein the plurality of optical zones comprises one or more diameters optimized to provide improved through focus visual performance based on one or more of the wearer's ocular optical characteristics, luminance, refraction, age, and vergence pupillary response.

11. The ophthalmic device of claim 1, wherein the tunable apodization mask comprises a first region corresponding to at least one of the plurality of optical zones having a first optical power and a second region corresponding to another the plurality of optical zones having a second optical power, wherein, upon receipt of a signal indicating a desired change in focus, the opacity of the first region increases or decreases and the opacity of the second region increases or decreases inversely to that of the first region.

12. The ophthalmic device of claim 1, wherein the tunable apodization mask resides circumferentially outside or inside at least one of the plurality of optical zones such that the transmissivity through the at least one of the plurality of optical zones approximates that of the bulk material of the lens irrespective of the desired focal length for the wearer.

13. The ophthalmic device of claim 1, wherein the tunable apodization mask is configured to permit at least 50% optical transmission through at least one of the plurality of optical zones irrespective of the desired focal length for the wearer.

14. The ophthalmic device of claim 1, wherein the tunable apodization mask comprises one or more fenestrations.

15. The ophthalmic device of claim 1, further comprising a rigid interconnect structure configured to create electrical connectivity between the tunable apodization mask and the processor, wherein the interconnect structure is composed of a translucent material and is dimensioned to include at least one void.

16. The ophthalmic device of claim of 1, at least one of the plurality of optical zones is decentered by an amount calculated to offset, at least partially, an expected decentration of the lens on an eye of the wearer.

17. A non-transitory computer-readable medium for use in an ophthalmic device comprising a lens comprising a lens body having a plurality of optical zones each having a paraxial optical power optimized for one or more focal lengths, the computer-readable medium comprising instructions stored thereon that when executed by a processor perform the steps of:
    receiving real-time focus data from one or more focus sensors;
    determining, based on the real-time focus data from the one or more focus sensors, a desired focal length of a wearer of the ophthalmic device; and
    actuating a tunable apodization mask positioned within at least a portion of at least one of the plurality of optical zones; wherein the actuating the tunable apodization mask-varies an opacity of the tunable apodization mask and thereby selectively increases or decreases a transmissivity of light through each of the plurality of optical zones to effect a change in optical power of the ophthalmic device.

18. The computer-readable medium of claim 17, further comprising the step of determining whether a change of focus is required by comparing a desired mode associated with the data to a current mode of the tunable apodization mask.

19. The computer-readable medium of claim 18, wherein the current mode of the tunable apodization mask includes at least one of a near-vision mode, a distance-vision mode, and an intermediate-vision mode.

* * * * *